United States Patent
Dai et al.

(10) Patent No.: US 7,449,569 B2
(45) Date of Patent: Nov. 11, 2008

(54) ISOLATED FUNGAL PROMOTERS AND GENE TRANSCRIPTION TERMINATORS AND METHODS OF PROTEIN AND CHEMICAL PRODUCTION IN A FUNGUS

(75) Inventors: Ziyu Dai, Richland, WA (US); Linda L. Lasure, Fall City, WA (US); Jon K. Magnuson, Pasco, WA (US)

(73) Assignee: Battelle Memorial Institute, Richland, WA (US)

( * ) Notice: Subject to any disclaimer, the term of this patent is extended or adjusted under 35 U.S.C. 154(b) by 300 days.

(21) Appl. No.: 10/920,625

(22) Filed: Aug. 17, 2004

(65) Prior Publication Data

US 2006/0040342 A1 Feb. 23, 2006

(51) Int. Cl.
| | |
|---|---|
| *C07H 21/04* | (2006.01) |
| *C12Q 1/68* | (2006.01) |
| *C12N 15/00* | (2006.01) |
| *C12N 15/63* | (2006.01) |
| *C12N 1/00* | (2006.01) |

(52) U.S. Cl. .................. 536/24.1; 435/6; 435/69.1; 435/320.1

(58) Field of Classification Search .............. None
See application file for complete search history.

(56) References Cited

OTHER PUBLICATIONS

Roberts et al. Expression of the *Escherichia coli* beta-glucuronidase gene in industrial and phytopathogenic filamentous fungi. Curr. Genet. 15:177-180, 1989.*
U.S. Appl. No. 10/442,017, Lasure et al.
Ebert et al. Proceedings of the National Academy of Sciences USA, 1987, 5745-5749, vol. 87.
Dai et al., "Identification of genes associated with morphology in *Aspergillus niger*. . . ," Applied Environmental Microbiology, 2004, 2474-2485, vol. 70.
Bennett and Lasure, eds., "More Gene Manipulations in Fungi," 1991, 441-458, Academic Press Inc, San Diego, USA.
Jefferson et al., European Molecular Biology Organization Journal, 1987, 3901-3907, vol. 6.

* cited by examiner

*Primary Examiner*—David Guzo
*Assistant Examiner*—Michele K. Joike
(74) *Attorney, Agent, or Firm*—Wells St. John P.S.

(57) ABSTRACT

The present invention encompasses isolated gene regulatory elements and gene transcription terminators that are differentially expressed in a native fungus exhibiting a first morphology relative to the native fungus exhibiting a second morphology. The invention also encompasses a method of utilizing a fungus for protein or chemical production. A transformed fungus is produced by transforming a fungus with a recombinant polynucleotide molecule. The recombinant polynucleotide molecule contains an isolated polynucleotide sequence linked operably to another molecule comprising a coding region of a gene of interest. The gene regulatory element and gene transcription terminator may temporally and spatially regulate expression of particular genes for optimum production of compounds of interest in a transgenic fungus.

18 Claims, 16 Drawing Sheets

FIG. 1A

```
  1  ATCCACAGCAGATGGATCATAAGCAGTCAGACTGCAGGTCAGGTATCGGA    50
  1                                                         0

51  GTCCGAGACATTCGAACTAGTCTCCGACGCCACTGGAAAAATTCCTGCAC   100
  1                                                         0

101  TCGCCCACACGTGGTAAGCGATACGACTACATATTGTGTGGACAGAGGAA   150
  1                                                         0

151  TGTGGCCTCGAGCAGAGAAAGCTTGCCAACATGAAGATCACTGGCAGGCG   200
  1                                                         0

201  TGCTCATGAAAGCCATTCCGTGGGTTTTGTTTGGATAACCCGCAAGGTAC   250
  1                                                         0

251  ATACTCCGGGAGTGCTTGTCTCTTCAAGGTTCGCAGTATGACGGATCATC   300
  1                                                         0

301  TCCCTTGGTACGAAGGAAGGCATGTTATCAGTTATCGTGCCTTGTTAGTG   350
  1                                                         0

351  GCATTGGCAGTCGGAACGAGGGTCCACTAACCCAGTCAGGAACGAGGAAT   400
  1                                                         0

401  GAGCGACAGGAACCAGAGAATCTTCACCCAACATAGCGATGGATGATCTC   450
  1                                                         0

451  ATCGAGGACGTTGATCACCTCTCTCGCGGGGACTTTCAACGACGAACGGT   500
  1                                                         0

501  CAGTTTGCAGAATGAAACCCCCTTGACAATCTGTTGATCTGCGGCCAGTG   550
                                       ||||·|||||·|
  1                                    ctgcagccagcg        12

551  GGAAGAAA----GGAGGGAGTACGTGG---------------GTAGTAAC   581
     |||·||||    |||||||·||||||                |||||||
 13  ggaggaaaaagggagggactacgtgggtagtagtagtagtagtagtaac    62

582  ATGACTTGTGTGTTTCTTGGTGTCTCTCCGTAGCAATTTAGGCGACCATC   631
      ·||||        ||·||·||||·||||||||||||||||||||·|||
 63  ctgac--------ttttttgtgtttctccgtagcaatttaggcgactatc   104

632  CGATTACACGGGGGTGGAGACACCGGACAGGTTCCTTGGTGCCTTT----   677
     ||||||||||||||||·|||||||||||||||||||||||||||||
105  cgattacacgggggtggggacaccggacaggttccttggtgccttttgga   154
```

FIG.1B

```
 678 -------GGAGGACACGAGATGCGTTTAGTGCCTCTGGTCCCAATATTCG       720
        .||||||||||||||..||..|||||||||||||||||||||
 155 ctttaggagaggacacgagatggattgggtgcctctggtcccaatattcg       204

721 GAAGGTGGTAATTAAACTCTGTGCCTGGCCACTTCGGTGATTTAACGCTT       770
     |||  |||||||||||||||||||||||||.||||||||||| |||||||||
 205 gaa-gtggtaattaaactctgtgcctgtccacttcggtga-ttaacgctt       252

771 CGGCCTCGTGGCGTGTCTATGTCTCATTTGTGTCAAACCAGGACGCACCG       820
     ||||||||||||||||||||||||||||||||.||.|||||||..||||
 253 cggcctcgtggcgtgtctatgtctcatttgtgccagaccaggactgaccg       302

821 GAAGCAGCTGGCAAGGCTCCGGAAGGCGAAGCCAATCAAGCACCACTCGA       870
     ||||.|||||||||||||||||||||||||||||||||||||||||||..|
 303 gaagaagctggcaaggctccggaaggcgaagccaatcaagcaccactta       352

871 TGAGGGGCACTGATCCATCCATTGTAAATTTTACATGAGGGTAATTTCCC       920
     ||||||||||||||||||||||.|||||.|||||||||||||||||||||
 353 tgaggggcactgatccatccatcgtaaaatttacatgagggtaatttccc       402

921 AGGTAATTTGCCCTGC-GGCTATGTCATTGAGAATGGAAAAGTCTCCGGA       969
     ||||||||||||||||  ||||||||||||||||||||||||||||||||
 403 aggtaatttgccctgcgggctatgtcattgagaatggaaaagtctccgga       452

970 TAATATTTGCCAAAAATGTGAGATGTGTGTGCGTG------------TG      1006
     ||.||||||||.||||||||||||||||||||.|.|.|                ..
 453 tattatttgccagaaatgtgagatgtgtgagagggggaaaaaaaaaaaaaa       502

1007 TGAAAACGCTCGAGCTTCTGGAAGTGAAACAAAAGCTGAAAGGA--AAGG      1054
     ..||||||||||||||||||||||||||||| ||||||.||||||    ||||
 503 aaaaaacgctcgagcttctggaagtgaaac-aaagctggaaggaggaagg       551

1055 AGGTG---GTGATGGCGA-TAATGGTGGTGGTGGTGGTGGTGTTTGTTTG      1100
     ||..|   |.|..|.||| .||.||.||| ...||.|||||||||||
 552 agagggacgagcagacgaggaaaggaggt--aaatgatggtgtttgtttg       599
```

FIG.1C

```
1101 TTTGTTTGCGCGCGAATCCCTTGCGGGCCAAGTTCCACCAAC-GACTTCT  1149
     |||       ·|||||||||||||||||||||||||||||| ·|||||
 600 ttt-----tgcgcgaatcccttgcgggccaagttccaccaacaaacttct  644

1150 CTTTCTACTGTGTCTCTTCGTACTCCGTCCAGCTGCTGCTAGCCATCAAC  1199
     |||||||     ·|||||· |·| ||·||||·|              ·||||
 645 ctttcta-----actcttt-ttc-ccttccatc-----------acaac  675

1200 AACATCCTTCCTTCTCCGTTCTCGGGGTTCCTCCGTTGTTCCTGGCCTGG  1249
     ||||||||·|||||||||||||||||||||||||||||||||||·|·|||
 676 aacatcctcccttctccgttctcggggttcctccgttgttcctgacttgg  725

1250 TCTGACATAAGGTTATGATTGTTTCACATGTCCCACGGCTTCGCCGGCTT  1299
     ||||||||||||||||||||||||||·|||||||||||||||||||||||
 726 tctgacataaggttatgattgtttcacttgtcccacggcttcgccggctt  775

1300 GGAGCTGAGACCCTCTTCTGAGTC-AATGGTACCATTTTGCCGAATTCGT  1348
     ·|||||||||||||||||||||||  |||||||||||||||||||··||||
 776 agagctgagaccctcttctgagtcaaatggtaccattttgccgatatcgt  825

1349 GGCTAGTTCTC-TATTTCTATGCTCTTGACTTTGGTACCGTTGGCATTAG  1397
     ||||||||||| ||·||·||·|||||·||·|·|||||||||||||||||
 826 ggctagttctcttacttttacgctctggattatggtaccgttggcattag  875

1398 TTTGATC-------TACTAATAAAGAGCCTAGTTTTAGGCGAATATACAC  1440
     |||||||       ||||||||··|||||||||||||·||||||||
 876 tttgatctattccgtactaataacaagcctagttttaggcggatatacac  925

1441 TGTTACCCACCGGGTAGTATTCAGTAGCTAC--CCTCCCACTCCCC--AG  1486
     |||||||| |·|||||·|||||||||··|||  |||||||||·|·|  ||
 926 tgttaccca-caggtagcattcagtaaatacctcctcccactactcttag  974

1487 GCTCCCACGCTGAGAGCCTTGATTCGATGTCTCTCCTAAAATTGCTAGGC  1536
     ||||||||||·|||||||||||||||||||||||||||||||||||·||||
 975 gctcccacgctcagagccttgattcgatgtctctcctaaaattgccaggc  1024
```

FIG. 1D

```
1537 TGTTAGCGCCCTGGCAGATGAACCCCCGCTCATCCCTCGTATATGCGG--   1584
     ||||||||||||||||||||||||||||||||||||||||||||.|||||
1025 tgttagcgccctggcagatgaaccccgctcatccctcgtatctgcggtc   1074

1585 --------TCTCAATTTCTGAGTGGCCCACGCCT-CCGAGTATCTTTGAG   1625
             |||||||||||||||||||||||| |||||||||||||||
1075 tcaatttatctcaatttctgagtggcccacgcctcccgagtatctttgag   1124

1626 CACATCCACGATGGAGGGAGGCGATCCAAGCGGTCTAACAGCGGACTAAA   1675
     ||.|||||||||||||..||||||||||.|||||||||||||||||||||
1125 catatccacgatggaggggagcgatccaagcggactaacagcggactaaa   1174

1676 CCGCTCTGTGTAAGCCAGTCAGAGAGTCATACTGGCTTGAGGTGACATCG   1725
     |||| | ||||||||||||||||||||||||||||||||||||||||||
1175 ccgc-c-gtgtaagccagtcagagagtcatactggcttgaggtgacatcg   1222

1726 CCAATTCATTTCACAAGGTTTAGTCGGGGGAGGGTAGGCCCCATACATTC   1775
     ||.|||||||||.|||||||||||||||||.|||||||||||||||||||
1223 cctattcatttcgcaaggtttagtcggggaagggtaggccccatacattc   1272

1776 CACCGTTCTCAAAGTTTACCAGGCATTTCTCACACTAACCATGCAATAGT   1825
     ||||||||||||||||||||||.|||.|||.|.|||||||||||||||||
1273 caccgttctcaaagtttaccagacatctcttagactaaccatgcaatagt   1322

1826 AGGTAACTAGCAGTAGTCTTGAACGCTGTTCCTGAGCAAGTTCCCAATCA   1875
     ||||||||||||||||||||||||||||||||||||||||||||||||||
1323 aggtaactagcagtagtcttgaacgctgttcctgagcaagttcccaatca   1372

1876 GCAATT----TGAAAGAATAATTTCCTTTGACCCACCGGGTAAATGAGCC   1921
     ||||||    ||||||||||||||.||||||||||||||| ||||||||
1373 gcaatttgaatgaaagaataatttcccttgacccaccggg-aaatgagcc   1421
```

FIG.1E

```
1922 GCAGATTTGGCGATGTTGGGCTCGGAGCCTGGTAGGTAGTAGTGAATGTC    1971
     ||||||||||||||||||||||||·||||||||||||||·||||||||||||
1422 gcagatttggcgatgttgggcttggagcctggtaggttgtagtgaatgtc    1471

1972 ATCCCCTCCATAGGGGGGAATT--GGGAGGGGGGCTGTGAATGGACTTGT    2019
     |||||||||||||||||||||||  |·||||||||||||||·||||||||
1472 atcccctccatagggggggaattgagagaggggggctgtgaagggacttgt   1521

2020 CCTACGCCTGTCGCATCCCCATCATTCATATACTTGAATG-TCTCTTCTC    2068
     |||||||||||·||||||||||||||||||||||||||||  ||··|||·|
1522 cctacgcctgtcacatccccatcattcatatacttgaatgttcctttccc    1571

2069 CCCCCTCCTCCTTCTCTTTCTCTCCTTCCCTTCTCACGATTTGACGTCCC    2118
     |||||||||||||||||||||||||·||·||||||||||||||||||||||
1572 cccctcctccttctctttctctcgttcccttctcacgatttgacgtccc     1621

2119 TCGCGTTTTCGCCCTCTCCCACGGTAGTCACTCCTTTGCACTACATACAC    2168
     ||||·|||||||||||||||||||||||||||||||||||||||||||||
1622 tcgcattttcgccctctcccacggtagtcactcctttgcactacatacac    1671

2169 GAAGTCTTACTTCCAGTCACTCTTTGAA-ACCACTTCTCAATATCCCTAC    2217
     |||||·|||||||||||||||||||||  ·||||···|||||||||||||
1672 gaagttttacttccagtcactctttgaattacactctccaatatccctac    1721

2218 CTCTTATCATTCTTTACTTCACGCACAAGACACGAAAGTgaacctgtaaa    2267
     ||··||||||||||||·||||·|||||||||||||||||···|·|||
1722 ctactatcattctttacatcacacacaagacacgaaagtgaaatcgaaaa    1771

2268 aatg                                                  2271
     ||||
1772 aatg                                                  1775
```

SEQUENCE LISTING

```
<160> NUMBER OF SEQ ID NOS: 61

<210> SEQ ID NO 1
<211> LENGTH: 25
<212> TYPE: DNA
<213> ORGANISM: Artificial
<220> FEATURE:
<223> OTHER INFORMATION: Synthetic Oligonucleotide

<400> SEQUENCE: 1
ccacggtagt cactcctttg cacta                                  25

<210> SEQ ID NO 2
<211> LENGTH: 26
<212> TYPE: DNA
<213> ORGANISM: Artificial
<220> FEATURE:
<223> OTHER INFORMATION: Synthetic Oligonucleotide

<400> SEQUENCE: 2
cctctattct gtctcccttc ggcgat                                 26

<210> SEQ ID NO 3
<211> LENGTH: 22
<212> TYPE: DNA
<213> ORGANISM: Artificial
<220> FEATURE:
<223> OTHER INFORMATION: Synthetic Oligonucleotide

<400> SEQUENCE: 3
gcaatcgtct tcccgtcgtt ca                                     22
```

```
<210> SEQ ID NO 4
<211> LENGTH: 25
<212> TYPE: DNA
<213> ORGANISM: Artificial
<220> FEATURE:
<223> OTHER INFORMATION: Synthetic Oligonucleotide

<400> SEQUENCE: 4
gtctgtcgtg gtgtcgtatc aaatg                                           25

<210> SEQ ID NO 5
<211> LENGTH: 24
<212> TYPE: DNA
<213> ORGANISM: Artificial
<220> FEATURE:
<223> OTHER INFORMATION: Synthetic Oligonucleotide

<400> SEQUENCE: 5
ctccttcttc cccccatac atca                                             24

<210> SEQ ID NO 6
<211> LENGTH: 24
<212> TYPE: DNA
<213> ORGANISM: Artificial
<220> FEATURE:
<223> OTHER INFORMATION: Synthetic Oligonucleotide

<400> SEQUENCE: 6
gctgtgcttc gtaccttcat ttcg                                            24

<210> SEQ ID NO 7
<211> LENGTH: 25
<212> TYPE: DNA
<213> ORGANISM: Artificial
<220> FEATURE:
<223> OTHER INFORMATION: Synthetic Oligonucleotide

<400> SEQUENCE: 7
gccatctatc aacacgagag aaaac                                           25

<210> SEQ ID NO 8
<211> LENGTH: 25
<212> TYPE: DNA
<213> ORGANISM: Artificial
<220> FEATURE:
<223> OTHER INFORMATION: Synthetic Oligonucleotide

<400> SEQUENCE: 8
tgcagatctt cgttaagacc ctcac                                           25

<210> SEQ ID NO 9
<211> LENGTH: 25
<212> TYPE: DNA
<213> ORGANISM: Artificial
<220> FEATURE:
<223> OTHER INFORMATION: Synthetic Oligonucleotide

<400> SEQUENCE: 9
ctctcccacc tccccagcct ttcct                                           25

<210> SEQ ID NO 10
<211> LENGTH: 24
<212> TYPE: DNA
<213> ORGANISM: Artificial
<220> FEATURE:
<223> OTHER INFORMATION: Synthetic Oligonucleotide
```

```
<400> SEQUENCE: 10
gagtcgacga atcgaatcga atcg                                          24

<210> SEQ ID NO 11
<211> LENGTH: 26
<212> TYPE: DNA
<213> ORGANISM: Artificial
<220> FEATURE:
<223> OTHER INFORMATION: Synthetic Oligonucleotide

<400> SEQUENCE: 11
gacaccatca cagacatata cagaga                                        26

<210> SEQ ID NO 12
<211> LENGTH: 22
<212> TYPE: DNA
<213> ORGANISM: Artificial
<220> FEATURE:
<223> OTHER INFORMATION: Synthetic Oligonucleotide

<400> SEQUENCE: 12
caaagagtgg ctgtagttgg ct                                            22

<210> SEQ ID NO 13
<211> LENGTH: 24
<212> TYPE: DNA
<213> ORGANISM: Artificial
<220> FEATURE:
<223> OTHER INFORMATION: Synthetic Oligonucleotide

<400> SEQUENCE: 13
gtgcccatca gaagtgaacc aaga                                          24

<210> SEQ ID NO 14
<211> LENGTH: 24
<212> TYPE: DNA
<213> ORGANISM: Artificial
<220> FEATURE:
<223> OTHER INFORMATION: Synthetic Oligonucleotide

<400> SEQUENCE: 14
gcattccagc tcctgtctgg acaa                                          24

<210> SEQ ID NO 15
<211> LENGTH: 22
<212> TYPE: DNA
<213> ORGANISM: Artificial
<220> FEATURE:
<223> OTHER INFORMATION: Synthetic Oligonucleotide

<400> SEQUENCE: 15
cacaagcgtc caatccatca ca                                            22

<210> SEQ ID NO 16
<211> LENGTH: 26
<212> TYPE: DNA
<213> ORGANISM: Artificial
<220> FEATURE:
<223> OTHER INFORMATION: Synthetic Oligonucleotide

<400> SEQUENCE: 16
gagatcgaca aggtaacatt ccagaa                                        26

<210> SEQ ID NO 17
<211> LENGTH: 25
```

```
<212> TYPE: DNA
<213> ORGANISM: Artificial
<220> FEATURE:
<223> OTHER INFORMATION: Synthetic Oligonucleotide

<400> SEQUENCE: 17
gcggaggaca agatggagag tagac                                          25

<210> SEQ ID NO 18
<211> LENGTH: 23
<212> TYPE: DNA
<213> ORGANISM: Artificial
<220> FEATURE:
<223> OTHER INFORMATION: Synthetic Oligonucleotide

<400> SEQUENCE: 18
ccaaggtaaa gcagatctaa tgg                                            23

<210> SEQ ID NO 19
<211> LENGTH: 26
<212> TYPE: DNA
<213> ORGANISM: Artificial
<220> FEATURE:
<223> OTHER INFORMATION: Synthetic Oligonucleotide

<400> SEQUENCE: 19
actttcgtgt cttgtgcgtg aagtaa                                         26

<210> SEQ ID NO 20
<211> LENGTH: 26
<212> TYPE: DNA
<213> ORGANISM: Artificial
<220> FEATURE:
<223> OTHER INFORMATION: Synthetic Oligonucleotide

<400> SEQUENCE: 20
ggtttcttta tcctgtccgt atgctg                                         26

<210> SEQ ID NO 21
<211> LENGTH: 26
<212> TYPE: DNA
<213> ORGANISM: Artificial
<220> FEATURE:
<223> OTHER INFORMATION: Synthetic Oligonucleotide

<400> SEQUENCE: 21
gacggtttat attcgaccac gcctca                                         26

<210> SEQ ID NO 22
<211> LENGTH: 26
<212> TYPE: DNA
<213> ORGANISM: Artificial
<220> FEATURE:
<223> OTHER INFORMATION: Sythetic Oligonucleotide

<400> SEQUENCE: 22
gctagtggcc ttcattgttg tatgag                                         26

<210> SEQ ID NO 23
<211> LENGTH: 26
<212> TYPE: DNA
<213> ORGANISM: Artificial
<220> FEATURE:
<223> OTHER INFORMATION: Synthetic Oligonucleotide

<400> SEQUENCE: 23
```
tgaatgtgta aaaggaggag gggtaa                                              26

<210> SEQ ID NO 24
<211> LENGTH: 26
<212> TYPE: DNA
<213> ORGANISM: Artificial
<220> FEATURE:
<223> OTHER INFORMATION: Synthetic Oligonucleotide

<400> SEQUENCE: 24
agtaaggcga aatgaaggta cgaagc                                              26

<210> SEQ ID NO 25
<211> LENGTH: 26
<212> TYPE: DNA
<213> ORGANISM: Artificial
<220> FEATURE:
<223> OTHER INFORMATION: Synthetic Oligonucleotide

<400> SEQUENCE: 25
cagcagcaga cattgtgatg tgatag                                              26

<210> SEQ ID NO 26
<211> LENGTH: 25
<212> TYPE: DNA
<213> ORGANISM: Artificial
<220> FEATURE:
<223> OTHER INFORMATION: Synthetic Oligonucleotide

<400> SEQUENCE: 26
gatgccctcc ttatcctgga tcttg                                               25

<210> SEQ ID NO 27
<211> LENGTH: 26
<212> TYPE: DNA
<213> ORGANISM: Artificial
<220> FEATURE:
<223> OTHER INFORMATION: Synthetic Oligonucleotide

<400> SEQUENCE: 27
gcggtcagaa gagacttgaa ggagac                                              26

<210> SEQ ID NO 28
<211> LENGTH: 26
<212> TYPE: DNA
<213> ORGANISM: Artificial
<220> FEATURE:
<223> OTHER INFORMATION: Synthetic Oligonucleotide

<400> SEQUENCE: 28
ctgtggagta gatgggcact cttgat                                              26

<210> SEQ ID NO 29
<211> LENGTH: 26
<212> TYPE: DNA
<213> ORGANISM: Artificial
<220> FEATURE:
<223> OTHER INFORMATION: Synthetic Oligonucleotide

<400> SEQUENCE: 29
cacccaccta gtaatgctta gccatc                                              26

<210> SEQ ID NO 30
<211> LENGTH: 26
<212> TYPE: DNA
<213> ORGANISM: Artificial

```
<220> FEATURE:
<223> OTHER INFORMATION: Synthetic Oligonucleotide

<400> SEQUENCE: 30
tttgtggttc gccttaatag agcttg                                          26

<210> SEQ ID NO 31
<211> LENGTH: 26
<212> TYPE: DNA
<213> ORGANISM: Artificial
<220> FEATURE:
<223> OTHER INFORMATION: Synthetic Oligonucleotide

<400> SEQUENCE: 31
atcatctgac gctgatgcaa tagttc                                          26

<210> SEQ ID NO 32
<211> LENGTH: 26
<212> TYPE: DNA
<213> ORGANISM: Artificial
<220> FEATURE:
<223> OTHER INFORMATION: Synthetic Oligonucleotide

<400> SEQUENCE: 32
ggacatggac atggatatga gtttga                                          26

<210> SEQ ID NO 33
<211> LENGTH: 25
<212> TYPE: DNA
<213> ORGANISM: Artificial
<220> FEATURE:
<223> OTHER INFORMATION: Synthetic Oligonucleotide

<400> SEQUENCE: 33
ctttagcacg gctcatctac ggttg                                           25

<210> SEQ ID NO 34
<211> LENGTH: 25
<212> TYPE: DNA
<213> ORGANISM: Artificial
<220> FEATURE:
<223> OTHER INFORMATION: Synthetic Oligonucleotide

<400> SEQUENCE: 34
ttgagctcga gtggaaaggt ctacg                                           25

<210> SEQ ID NO 35
<211> LENGTH: 22
<212> TYPE: DNA
<213> ORGANISM: Artificial
<220> FEATURE:
<223> OTHER INFORMATION: Synthetic Oligonucleotide

<400> SEQUENCE: 35
gtaatacgac tcactatagg gc                                              22

<210> SEQ ID NO 36
<211> LENGTH: 19
<212> TYPE: DNA
<213> ORGANISM: Artificial
<220> FEATURE:
<223> OTHER INFORMATION: Synthetic Oligonucleotide

<400> SEQUENCE: 36
actatagggc acgcgtggt                                                  19
```

<210> SEQ ID NO 37
<211> LENGTH: 35
<212> TYPE: DNA
<213> ORGANISM: Artificial
<220> FEATURE:
<223> OTHER INFORMATION: Synthetic Oligonucleotide

<400> SEQUENCE: 37
tcaagcttct gctccaacgc gctatcaaat cgaac					35

<210> SEQ ID NO 38
<211> LENGTH: 36
<212> TYPE: DNA
<213> ORGANISM: Artificial
<220> FEATURE:
<223> OTHER INFORMATION: Synthetic Oligonucleotide

<400> SEQUENCE: 38
cacagctgat tgaaagaata gagagtgatg gagttg					36

<210> SEQ ID NO 39
<211> LENGTH: 40
<212> TYPE: DNA
<213> ORGANISM: Artificial
<220> FEATURE:
<223> OTHER INFORMATION: Synthetic Oligonucleotide

<400> SEQUENCE: 39
cggaattctc tagagtgatg tggataggga tgggaataag					40

<210> SEQ ID NO 40
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 40
ccaagcttat cgatgttgta gaagcgcagt taatggtgta tg					42

<210> SEQ ID NO 41
<211> LENGTH: 33
<212> TYPE: DNA
<213> ORGANISM: Artificial
<220> FEATURE:
<223> OTHER INFORMATION: Synthetic Oligonucleotide

<400> SEQUENCE: 41
atcccgggta aagcaaggcg aatgacgaag aca					33

<210> SEQ ID NO 42
<211> LENGTH: 30
<212> TYPE: DNA
<213> ORGANISM: Artificial
<220> FEATURE:
<223> OTHER INFORMATION: Synthetic Oligonucleotide

<400> SEQUENCE: 42
cagagctcct cctgtctgag tgttgtctca					30

<210> SEQ ID NO 43
<211> LENGTH: 33
<212> TYPE: DNA
<213> ORGANISM: Artificial
<220> FEATURE:
<223> OTHER INFORMATION: Synthetic Oligonucleotide

<400> SEQUENCE: 43
ctcagctgtt gtatgagagg tgtatatgta tgt                               33

<210> SEQ ID NO 44
<211> LENGTH: 30
<212> TYPE: DNA
<213> ORGANISM: Artificial
<220> FEATURE:
<223> OTHER INFORMATION: Synthetic Oligonucleotide

<400> SEQUENCE: 44
gcacgtgaat gtgtaaaagg aggagggta                                    30

<210> SEQ ID NO 45
<211> LENGTH: 20
<212> TYPE: DNA
<213> ORGANISM: Artificial
<220> FEATURE:
<223> OTHER INFORMATION: Synthetic Oligonucleotide

<400> SEQUENCE: 45
taatacgact cactataggg                                              20

<210> SEQ ID NO 46
<211> LENGTH: 2043
<212> TYPE: DNA
<213> ORGANISM: Aspergillus niger

<400> SEQUENCE: 46
aaacctaatg aaaataacat gaatctcagg attatacca tatcgactgt atcgcatcct    60
tctcattttg gccccttga ctcgcaatca tcgggagccc acgagtccgc tgcgggacgc   120
cggctcgctc ccaatccttt gccccagggg tcaaatgagc agtcctctat gacagtggga   180
agccacgccg gtcaggccaa atattgagag tcgagagtta gttatctgat ttcgtcaagc   240
ctgccgatcg cgcagaaact ggtagcgacc taggaccggt ggaccgccag ttaggagggg   300
actgcgaggg tgcgaagata aagtgaaaca tcccgatcgg ataaatgggc cgtgcagacg   360
ggggaccaat cagcttacgc agcccagggg atctgcatag gccacgccaa gctgctccaa   420
cgcgctatca aatcgaaggc ttgaaacgaa cagatgccat aatccgacag ccgtttgttt   480
cattcagagt agctcgctag catggtgacg actggtccag gccccatttg tcgtcatctt   540
gggccattcc atccatcacc ttcaactctg ccatgcagga aaccatggat agcctagcaa   600
aaccccggca tggacagatg ccagcgaaga cttccaccct acactagggt cccctcaggg   660
tcccattcct gttaatcccc ctattattgg gtccaccttg tgagctcccc caactttgac   720
ggggaaagct ctattccgag ttcggctaca acgttccag cgagggcatc atgtaaaacc   780
tcataaaaac gacttttct gatggatagg cagtgcaggt agaggaatga cttcccca   840
cagtgattat catgtttgtc ctgaccatag cttgcaggat gatctgtaag cgggagagga   900
ttatgctgca cgtagaggac actgaccaca acttctgttc ctcgagatgg acccacccaa   960
ataacgtaga gtcaaggacc cgccatcgtt gggcccccaa gaacacacca gagctgacta  1020
gccttccgct tagttagcac tacgacctgt cgactgtcag tgtcgagagt cgagactggg  1080
ctgacccacc aacttggaac cgccacagcg gcagggggaca gcttgatcga ggacgtcagc  1140
tccctggcac gctggttgcc attggataga gattatcaac cagttgaatt catccaccga  1200
cgatctgagg cacttttga ggcttttccca gtgagtccac tgagtttggg tggacgatgg  1260

```
gtagagagac aaccagacga agcattacca agggactcat gacggaaccg caaatagacc    1320
accaacaaca gccgcagcca ggatcaagcc acctccaaga ggcagggggg ccaaggagag    1380
ggacagtcga gtcatctatt ctgaataggc gatgaagaga tgaaacgctg gagtgtcggc    1440
tggcctgtga ctgcttccag ggcgagccgc gcacgtgggg ccgccacaga cagccagcca    1500
gacttcttcc cttctcttcc tatccatcaa tagcatcctc tacctacata ctcccttctc    1560
acagatccaa ctaccggctt catgcttagc cgacccacag aagcccagca ggtacgttca    1620 aaccctatt tgcatcagcc ctgcccctga gccactctac cacccccac aagcgccggg      1680 tctgccgatc cgtgcggttc ttgcatgtcc agcataacct gatctattgc tgacagtcga    1740
cgtctcagat gcaggcgagc cgaattcggt gacaacagtg catgacgaat gcttggttct    1800
ttccacgcat ctcaccagat ggatggaggt catcatcgct gggtcactgc cgacccagcg    1860
cttggagagc gccttataaa agcctccctt gccccagcca ggatcattcc tcattcagct    1920
caaattctct ttcctttgat ctcaactacc attccttaag aagctgtgct tcgtaccttc    1980
atttcgcctt acttttttc tgcttactac tacaactcca tcactctcta ttctttcaat     2040
atg                                                                  2043

<210> SEQ ID NO 47
<211> LENGTH: 1565
<212> TYPE: DNA
<213> ORGANISM: Aspergillus niger

<400> SEQUENCE: 47
ctgacgttga cattgaacgc tccatcaacc aaggagttgg gggtatcgag tttcatccct      60
atggggccaa acaattagca atgcttaatg cttgtgcaga aaataagcac accgggaatg    120
cgaggaaccg acagcctgca ttaaactgtg cttcggaaat tttatttccc tcctctgaga    180
cagtctcatt gatccttctg aaaatttatc cgatgggatt tccacagcac gctgtgctgc    240
ctatcgtgga tgctcgcacg gaagtttcta tatcctgatc gttaagcagg atcatgttct    300
atatttatca ctcatggctg agctgctctt agacatatca accgcactaa aatggcgatc    360
agagcaacaa ttaacaatgc cgaggatatc gatttgtcgc ctgattttg agtaagtttg     420 tctatttta ctcggtgaaa cagcgtctca gccaggaacc gttacgagta cgacacagcc     480
aacacgggcc ataacaaggc gagcccctga tcctcggggc cccgtcgtt cacgagccga     540 ggtgatcgct aagcgggact cgcggatcaa caggcgcgac cgtgtttcag atgtcaccat    600
gacaaggtgg ctatgagtaa ttccaggcga cgtgccgtgt gttagtgcca tgcggcaatg    660
atgggccgcc aagagtagtt ggggatgcag tggagagaga gagagacaac tcatacccag    720
atttgattca ttacttcagt acgtgcagac atgacatctg ataaaaccta ttccgaccga    780
gtcgtggttc tagaccggcg ggcttggcga ccgcaacacg acctttgcgt acattccaga    840
cgacgaaaca ctgcatcagg cacgggcatg ccggatcgag cgagacccctt gacagaattt    900 ggggcggccc ctgatgatgt gcggcctcaa agcgtcatca cccatttcaa cctgccagga    960
acagcaacgt tggagccaat cgcggatgca aatctggctg cctagaatag caattgccac    1020
ggcctcagcc cccgtgattg cgcggcccaa caggccttcc attggctgaa accccggata    1080
agccttgggt tttgtgcagt agtggaagct tggcaagtta ctgagccaat catattcctc    1140
taattcctcc aaggagggtg ggggcctgct aacgtcacgg acctgcttcc attgccttcc    1200
cctctgcccg tccttccatc ccagcccggt cggccgcgtc acagaccagg ctggaaaggc    1260
aacaaggctc gcaacctcat gcccatcatt ggctggtcct gcgtgatgct gcaggtcagc    1320
```

```
ttccaaactc agtcgcccat gctgaccttt ttttatgcag ccgggctgct tctttcattt   1380
ataggtcccc gtctggcatg tgtcttccct tccaacttcc cgactcactc cacctttcct   1440
catctgtcat ctgtacctag attccttctt atatcttatc cgtggttcct tcttttctgg   1500
ccaagatctt agccatctat caacacgaga gaaaacttat tcccatccct atccacatca   1560
caatg                                                                1565

<210> SEQ ID NO 48
<211> LENGTH: 982
<212> TYPE: DNA
<213> ORGANISM: Aspergillus niger

<400> SEQUENCE: 48
ctggagagga tccccttccc ccatcttccg ataagggatg cccccaactc acacgtcatc     60
gccgttgctg ccgccgcaag gccagttgtc gcattactcc ctgatcacca ccagtttgcc    120
tggtgagagg atacgaacaa ttatgagcaa ttcttcggag tagcaacgag tattttcacc    180
gggagtttca acgggttcta tttcaggaac acggctgcgg tctggattgg gtcgggctga    240
gataccgact ggtggcgtca gtggcgggta cggacggagt cgtcctggcc gctcgtagac    300
actcccccgg actgatatca ggccccggca actggcttcg tctcactcca gggcatcagg    360
agtgcctacc acatgggttc aggctttgcc ccgtcgtcta agtttgcagg acaaaatttt    420
cgtatgcgtt accactcttt cctttcagca accattccgt agtgaaaacc caataatagg    480
tggctgccgt gggagcctga gtcaacccaa ccagaacctt tctagtagat ctcccccaa     540 gcgcttcagc aacgaagcgt attggagaac caaatgacgc agaccaagcg gattccggtg    600
caatagccga atggcaaggg aatccccag gaggtgccag aagcgtcgcc cgaaaggtac     660
ttcgtctgac aggctaacac cgctcgggct aaggtccctg ctgctctttt ccctttattg    720
cgacttaacc tctaagccat tcccttgcat cacgttatct cactgaccga cctctgacta    780
aggcgcttcg cctccgccgc ctcccctcat tcacctcctc tcctgactgc ttaagccttc    840
tcttccttcc tctcactacc aaccctcctt catccctcat acctctcatc ctaccactca    900
cctttcgcgc atcgccatct gcgatcctcc ccacaacact ccacctagat acatacacca    960
ttaactgcgc ttctacaaca tg                                             982

<210> SEQ ID NO 49
<211> LENGTH: 748
<212> TYPE: DNA
<213> ORGANISM: Aspergillus niger

<400> SEQUENCE: 49
atacacctcc attaaagtag ggggaataag tcggatacat ccactggacc gatcaactgc     60
aggtatccgc accgctgcag gaacaaccac cgcaaggtta cccccggacg cttgctgtcc    120
agtcactgcc aaccgccagg cacacgggct gaataatggg cgtcaatatt tctctgtccc    180
actgtccctg agcgacacac ggtacccgcc cgatgacgtt ccatgggtcg gccgcggtga    240
ggatgcaggg gggtcaggaa cgctccgacg caggcaatca gaggggtcc gccgaacaat     300 ggaaaaagca acgattagtg actagttcga ctatactcat gcaagagcaa aaagaacct     360 tcctcttgtg gagacctgat tggtcggaac caaattggcg cctagaaaaa gcacccagcc    420
ctaacttggt tctgcaactg ccactccccg ttgtttgggcg tctatataac cgccctcttt    480
cccctccctg tctcctcttc gaaactcttc ttcctcgcct agatcttcct ctcccacctc    540
```

```
cccagcctttt ccttctttgc acctgtgccg tgcacggtcg agccattcct ccattctttg      600
aacatattgc ctggctccga gtagtctagc atccactcct tgcaagagca ctttgagaga      660
accggtcttc tcatactcaa aagttataca tacacatcac ttctctccga acaaaaccga      720
acagaattcg aagaacacat acacaatg                                         748
```

<210> SEQ ID NO 50
<211> LENGTH: 2271
<212> TYPE: DNA
<213> ORGANISM: Aspergillus niger

<400> SEQUENCE: 50

```
atccacagca gatggatcat aagcagtcag actgcaggtc aggtatcgga gtccgagaca       60
ttcgaactag tctccgacgc cactggaaaa attcctgcac tcgcccacac gtggtaagcg      120
atacgactac atattgtgtg gacagaggaa tgtggcctcg agcagagaaa gcttgccaac      180
atgaagatca ctgcaggcg tgctcatgaa agccattccg tgggttttgt ttggataacc       240
cgcaaggtac atactccggg agtgcttgtc tcttcaaggt tcgcagtatg acggatcatc      300
tcccttggta cgaaggaagg catgttatca gttatcgtgc cttgttagtg gcattggcag      360
tcggaacgag ggtccactaa cccagtcagg aacgaggaat gagcgacagg aaccagagaa      420
tcttcaccca acatagcgat ggatgatctc atcgaggacg ttgatcacct ctctcgcggg      480
gactttcaac gacgaacggt cagtttgcag aatgaaaccc ccttgacaat ctgttgatct      540
gcggccagtg ggaagaaagg agggagtacg tgggtagtaa catgacttgt gtgtttcttg      600
gtgtctctcc gtagcaattt aggcgaccat ccgattacac ggggggtggag acaccggaca      660 ggttccttgg tgcctttgga ggacacgaga tgcgtttagt gcctctggtc ccaatattcg      720
gaaggtggta attaaactct gtgcctggcc acttcggtga tttaacgctt cggcctcgtg      780
gcgtgtctat gtctcatttg tgtcaaacca ggacgcaccg gaagcagctg gcaaggctcc      840
ggaaggcgaa gccaatcaag caccactcga tgagggcac  tgatccatcc attgtaaatt      900
ttacatgagg gtaatttccc aggtaatttg ccctgcggct atgtcattga gaatggaaaa      960
gtctccggat aatatttgcc aaaaatgtga gatgtgtgtg cgtgtgtgaa aacgctcgag     1020
cttctggaag tgaaacaaaa gctgaaagga aaggaggtgg tgatggcgat aatggtggtg     1080
gtggtggtgg tgtttgtttg tttgtttgcg cgcgaatccc ttgcgggcca agttccacca     1140
acgacttctc tttctactgt gtctcttcgt actccgtcca gctgctgcta gccatcaaca     1200
acatccttcc ttctccgttc tcggggttcc tccgttgttc ctggcctggt ctgacataag     1260
gttatgattg tttcacatgt cccacggct cgccggcttg gagctgagac cctcttctga      1320
gtcaatggta ccatttttgcc gaattcgtgg ctagttctct atttctatgc tcttgacttt     1380
ggtaccgttg gcattagttt gatctactaa taaagagcct agtttaggc  gaatatacac      1440 tgttacccac cgggtagtat tcagtagcta ccctcccact ccccaggctc ccacgctgag     1500
agccttgatt cgatgtctct cctaaaattg ctaggctgtt agcgccctgg cagatgaacc     1560
cccgctcatc cctcgtatat gcggtctcaa tttctgagtg gccacgcct  ccagtatct       1620 ttgagcacat ccacgatgga gggaggcgat ccaagcggtc taacagcgga ctaaaccgct     1680
ctgtgtaagc cagtcagaga gtcatactgg cttgaggtga catcgccaat tcatttcaca     1740
aggtttagtc gggggagggt aggccccata cattccaccg ttctcaaagt ttaccaggca     1800
tttctcacac taaccatgca atagtaggta actagcagta gtcttgaacg ctgttcctga     1860
gcaagttccc aatcagcaat ttgaaagaat aatttccttt gacccaccgg gtaaatgagc     1920
```

-continued

| | |
|---|---|
| cgcagatttg gcgatgttgg gctcggagcc tggtaggtag tagtgaatgt catcccctcc | 1980 |
| ataggggga attgggaggg gggctgtgaa tggacttgtc ctacgcctgt cgcatcccca | 2040 |
| tcattcatat acttgaatgt ctcttctccc ccctcctcct tctctttctc tccttcccttt | 2100 |
| ctcacgattt gacgtccctc gcgttttcgc cctctcccac ggtagtcact cctttgcact | 2160 |
| acatacacga agtcttactt ccagtcactc tttgaaacca cttctcaata tccctacctc | 2220 |
| ttatcattct ttacttcacg cacaagacac gaaagtgaac ctgtaaaaat g | 2271 |

<210> SEQ ID NO 51
<211> LENGTH: 1680
<212> TYPE: DNA
<213> ORGANISM: Aspergillus niger

<400> SEQUENCE: 51

| | |
|---|---|
| atcctgaggt tgccaccatc aagtgcttgg tctgtttcca aggtacacat attctgcgta | 60 |
| gtggactaga acatccactt actacgtcgt tggagccgat gcggaggcca agcttcgtgc | 120 |
| ttgggaaaca agcaacaggc caagcaacga gtggatgggt cttggagcca ctgagcggtc | 180 |
| atgccgtcca tgggactggc ctcgatagta gaaggtcctt ctgataagcc cgtgtgcaca | 240 |
| gggcctcccg ggtttccggc tagtccatgc cacaggtttt tcttcactcc tttccctcac | 300 |
| ccctggccac ccatctgagg ttcatccaat cggtgacccc cgagaatgtc tccgcgctac | 360 |
| catagtagta tctagcactc ttagctactc ataagcgaca agtcttttg ggtttcgtgc | 420 |
| cgctatggct ggaaccatta attccggacg taggagcgtt gcagtcaggt agattgttgt | 480 |
| gtaagggaaa ttggtccatg aaaatcggca aaattgatgg gaagcaagac aagggagcgc | 540 |
| tagtgcagcg gtcgcatggt cacggttccc ccatccactc ggttctccgt cggcaatttc | 600 |
| tgtctttcct ttccctttg tcgttccctt cactttattg gggttattta ttgattctgg | 660 |
| taataatatt cgctcttatc ttcccccaac cgtcacgaaa atgggccttg gtccgatgtg | 720 |
| tgtgcatcca caaccgacca cccacaccac tacctcgtcc tcctccttcc ctataggcca | 780 |
| acattgcctt acggtgtatc ggacggtgct ccagatcgaa atttgcgatc caataagtcc | 840 |
| cctgcagaca ctaatcaagg tcaggtctca ttgggcgcga taacgtgctt cggccaggca | 900 |
| atcacactca tgaccatatt cttgctcatc ctcatcctca tccacatcat atcatcagga | 960 |
| tttcagtaag gtcagcagca tccgactcca gccgcagcaa gcctgtgacc ctggtctagt | 1020 |
| ctgcaattct ccgaacaaac gagcgtgttg acggtggagt ctcctggttc gtggcaagcc | 1080 |
| gttcgtgcag cccacggtta tctggtgtgt taccctccta aatcagttaa ccaagacgcc | 1140 |
| acccctcctt cggaccttcg acagatgctc cagaagacct cgatgtgcca atcaagttcc | 1200 |
| tgactagcgg tgatggcctc ctcaaagtgg ggagatgcag accgtttaag tttccactgg | 1260 |
| accgtcaatg gcattctgaa tgggtgccca ccgtggctcg aacatcgctg ctactggcgt | 1320 |
| tgattaaatt gcatcgataa ccagtgctgg atcagctcat actgacggcg ataatgtaga | 1380 |
| tactagccca cagtaatcca tcggattccg cctgctaatt ccgctcctcc cattcccatt | 1440 |
| tgtccctttg gttattagct agtggacgtt atctccccg tcagcctccc attgactggt | 1500 |
| ctggcaccca ctaccagcta ctctgtagtc tcgcgcccc gtcgcgtgct tgctgcttgg | 1560 |
| cccttcttaa gcaccgccga tcccacctcc cccagttctg gatctttgca cccctcaagt | 1620 |
| tcgtcctcta ttctgtctcc cttcggcgat tgtcttcgtc attcgccttg ctttaccatg | 1680 |

<210> SEQ ID NO 52

<211> LENGTH: 2344
<212> TYPE: DNA
<213> ORGANISM: Aspergillus niger
<400> SEQUENCE: 52

| | | | | | |
|---|---|---|---|---|---|
| taatacgact | cactataggg | cacgcgtggt | cgacggcccg | ggctggtctg | gcagatatat | 60 |
| gtttagaaac | tgtccgaatt | tcgagaacag | acggccggtc | acacagagac | gtcgtaatcc | 120 |
| ctcgactgcc | ctcacgcatc | ctggtggacc | gattgtccgg | gtgacgcaga | tcgaaacctt | 180 |
| ctgctgattc | ttagctgtgt | agcgtccagg | aaccggtgac | ctccgtacca | tggctcggtt | 240 |
| tcaatagtac | ccggcagtcg | gcgacgcgca | ttgctctcaa | gattgagtag | gatacctaag | 300 |
| gattgtaaac | catgatgaca | ttctttgtgc | gtagtcgagg | ttcaatctca | tgatctggcg | 360 |
| gacgacaggc | catgggtacc | tgcctacgga | ctatgcacga | ctgctgtctt | gtgtccgatt | 420 |
| ggcggacaat | atccctcccc | tagcagtact | ctgtagtgcc | gcagtgtgca | gtaatgtact | 480 |
| ggtgtaatgc | tccacgcaag | ctctggatac | ataccactat | atcctaaacg | caaaaccttt | 540 |
| gaatagaacc | acttcttttg | gatgatggat | cccacatggt | ctgactatat | attctgctgc | 600 |
| gcgtcaagcg | gctatctcac | tgtctgacac | tgagtcgctc | gtcgtcagcc | catggcgttt | 660 |
| gagtcggtta | gttttgcttg | ccgaaggtct | agccgagtct | ctgcccgaat | gtttcccgcc | 720 |
| ctccgccaat | cccacggccg | atggacagcc | tcaggctgcc | ttcagcccca | tggatgccgt | 780 |
| gttgcctgag | gaccttgcag | cgggcgctat | cacatgattg | tgtcacagca | agcaatgagg | 840 |
| agcagatcat | gattagtgta | cttagcttga | accctactac | taaattgcac | acagtcattg | 900 |
| gaacaccaca | cacagtgcaa | tggtggggac | aagcgccaaa | tagactcgtc | tccttttcac | 960 |
| aatccaggca | gcagtcctgt | tgggccgttg | tgcacgcatt | accgatggaa | tagtccaggg | 1020 |
| gtcgtgatcc | taccacggct | cgtctgccga | gctctccgct | gctccctgc | ccacacacca | 1080 |
| cgagcttcct | gtcgagcttg | cttgcccgtg | gcaattctga | ttcgttctga | tgcattatat | 1140 |
| ctcatgacta | ttcttctcct | atgaagtagc | ctcctggcat | atattctgca | atattaactg | 1200 |
| gcacaagtct | cgcttcagtc | tggtgtcagc | gtcggcaatc | aactcctcat | tatcgcgatt | 1260 |
| cgcgggcgga | gccccgcgac | tccgactgcc | tgctagtaac | cgacccacca | tcgatgatgg | 1320 |
| atggagccca | ggccacattc | cgtcccgggc | caggggggtc | cggtgccagt | ccttgagttc | 1380 |
| aactgtcttc | gtcccatctt | taggacaccg | ctgctgggct | tcttcctggg | gataatcatg | 1440 |
| gcacccatga | ttctatctcg | ccgttcgtgg | gctagcggca | ggccaatgcc | gggaacggca | 1500 |
| cagcgggcct | ttatcgagac | actgccaggc | tatggcagag | ttgtatagcg | gaatggccat | 1560 |
| tttgagctgg | aaggaataga | ttcaaggtac | tcgagagtca | caatccgtaa | gccacattca | 1620 |
| ctccgtatca | ttatctagcc | tctcattcac | cagtcaaact | catgagtgtc | cggtagacat | 1680 |
| aggcacgatc | tgctcaccgc | aattgtcatt | tgtgggatgt | gctggacata | cttggccatt | 1740 |
| tacgctttta | cgcgggcgct | cggaagtcaa | cacctcgcta | gacaatccct | gaagcctgtc | 1800 |
| atttgccagg | aaggtggact | agtgcactgt | tgagctggtt | gggggtgcgg | agcagtttgg | 1860 |
| atccggatac | ggtcagcaac | gtgacccgcc | gtataagtac | cgctccctcc | tcgctttccc | 1920 |
| tcgacccttc | ctccttctac | cacccatcaa | taccttcagt | tcgttagcaa | tcgtcttccc | 1980 |
| gtcgttcaat | tcaacttctg | atcacactct | ctgaggcgtg | gtcgaatata | aaccgtcaaa | 2040 |
| attttcgcca | cacttcttaa | ctcgtaagtt | ccccaccatt | ctccgcggtc | tcccgacgat | 2100 |
| ggctgccct | atcccagtgc | tccaggaaca | gcaattggac | cttcctccaa | gcaatcccac | 2160 |
| tttccagggt | cttcttatgg | ctaatctgtc | tcctttcctt | taggcggcac | cacccgttca | 2220 |

```
acggccggcg ctcatccaac cgtggtgggg caccggacta cgcattatac gtccagtaaa   2280
caactcgcag tctgaacact cgtattatct gtctcgcacc ccaatctgtc aactgtgaac   2340
aatg                                                                 2344

<210> SEQ ID NO 53
<211> LENGTH: 1838
<212> TYPE: DNA
<213> ORGANISM: Aspergillus niger

<400> SEQUENCE: 53
cctcgatccc actctcccca ccctcctcct gtctgagtgt tgtctcatat acctcacccc     60
cagcgaagcc agcttggtag tccgccactt cacagaaacc atctttccgg cgaccacgcc    120
ggtagggttg gttctgtatg agcccatccg gccagacgat gcgttcgggc gcacgatggt    180
ggcgaatcta gccacgaggg ggattcagtt gcagacattg caggagtatg cgtcgctggg    240
ggcgcagcga cggaggttac gggagatggg attggacggg gggcaggcgg cagcagatgt    300
agatttcatc tgggaaaggt gggtgagtga gcgggagaag gaacgggtgg cagggttgga    360
gatgttggat gagatggagg agtggcagtt attggcaaga cattattgtg ttgcatgggg    420
gtggagggat gttcctggtg gagtgtttga gggatggagg gagatggaag ggcaggagga    480
gtaagagtat agtaagtata gtagtagtgt gcgtcatacg tgatggctag ctagctagtt    540
agtttgttgt acctaagtag ttccctagac tatcatataa ttattatata tgaatgaaaa    600
tccacgttga acgcttcgga gcgcacaggc caaggggcga gaaagaggag aagaagtgga    660
atcctgatgg aaaaaatggc agtccaagca acgtgcatgc aaccacctca ggacccctgt    720
ctattgaatt attattattg acaattattg cctgatttca tggtactcga cagggtataa    780
tggcagtttg cctagcaatc atttcattcg tgcaatcaaa cctgacggta gatacgagcg    840
aacgagcaag cgagagacag actaaacata gactattgcc taagctagca ctgtagctcc    900
ccgcctctgt gtacaattgg cttgcgtctc cccctttttc aaactgccaa agtccgtgcc    960
ggtcagtgac tgagactagc tcagaggcag aggcactgac tcgattgaac tcgagcacta   1020
ctttctggct tatactggaa taggatgctg atccggtctg gacgtgtgct gatcgtgatg   1080
tcttgactgg gagaggaagg gagtggttga gagtttgtcc cgtgtcatat ttcgtagagt   1140
tgagttgact tgacagcagg caataattat agatttgagc tggataagat ttaacagaaa   1200
tttctgtata ctctctatcc cccctctctg tgtctatact gtatcctttg cgtgagtgat   1260
cccaccaagt atgaagagt gtctcaaagg gtccacggac cccttatcca tccatcagga   1320
acagtacggt aacctacact attccactat ccccaaagaa gtaatctacg gggggtattc   1380
catgaactgc cgcagtgcaa aggccgctga ttggcgtgac cccctgagcg ggtcatgcct   1440
gattgggatc gaagctttaa ggctatccac attgggtaac ccggggagag catcactttc   1500
aggctactag cagtagacta gtagtcttct ctagtcctgc tggctggtgg ttgtgggttt   1560
ctcttttctc ttgtcttttc cctcgttctt ctctcttttct tctcttcttt ctttctctgc   1620
ttcggtccag tctctcgttc ttgtctttac tgaccctagt ctttcgtttc gcgtggtctg   1680
tcgtggtgtc gtatcaaatg attattatta tcttctaacc tatccctctg cctatttgct   1740
atatatcccc aaaactgacc catacatatc acatctctcc acctttggtt acatatacat   1800
acattcatac atacatatac acctctcata caacaatg                           1838

<210> SEQ ID NO 54
```

<211> LENGTH: 1506
<212> TYPE: DNA
<213> ORGANISM: Aspergillus niger

<400> SEQUENCE: 54

```
ctgataactc ttgcctggcc attacgacga tccttcgtcc attcgagtga gtaactgagc      60
catggtggaa gggaaaagtg tggaaagagg gagaagacga ggggcatgcg acactcaaag     120
cctacggatc gggcaagacc atcagacaag cctatctatc ctgtgtggtc tattagatat     180
gccatctgat ccgaaacaat aacccgtaaa agatactcc gagtccagac ggagttttcc      240
tcgcaagcag gtttgtcgtc atgggcaatc aatggccggg acgcagggga gagacaaagg     300
ataccaggga acgcatccca ttgccgtgtt aaagtgcttg catcccggg acagaggggg      360
tacattgcgg gtttacatca tgtgtctgca gttaagctgg attgtgtaag tagggtaata     420
ttattgcagc agtgagctcc aaaaagtacg gtggtgtgga gattgaatcc tcacgttcat     480
atcggtcagt gtgggagagt aacatgggcc gatgttgatc gagggcgggt gtatagttag     540
ggtgaatgcc atatcacaga acatggcggc aagagccggt gaaaaggaaa aggcaaaaaa     600
gaatcatcca cccggagcaa gatgagctgt cggtaagacc acttggagct aggttgtgca     660
atgatgcgtt gggtgtgaga gctgtggttg gaggcagccg tatcctgctc ccccgttttc     720
gggacatagg atgaagagta cggcgtatac cagatcctgg acaccatcag attttctccc     780
tctcaacaat tgtggaaatt aggaggtgga tcgttctgag ttgggagtcc tgtccggtga     840
aacttcccat ccacaatttc gaccccttt cttctcccg tcatggggga gaaatggtgt      900
atcgtcgaaa gaagtttgtt gatatgatgc gccgtgactt cgatcaccca aagaccatct     960
atactataga tctgaggcgg cgtgactgcg agaacaccgg cgggacaacc tcaggcaccc    1020
cagggcaggc cagggcgccg accaaccaca gcttgcagac tgagccagac aggcccacca    1080
ggccacgcac tagaagcaca ctaaaaaagt agctgatccg taagtattgt ctggctgcat    1140
aggaacgggg gccgacccag ttcgttgctt tttttttttc ttttttttctt ttgcctccgg    1200
ccgatggtca gtgaccacct gggaaaccgt tcgcccgctg gtctcgggggg ggatcctcta    1260
gtatatcgtg agcttcacta cttatactct cctctttcac cttctctcaa gctccttttt    1320
tctttctctc tcctccaaca aattttctc ctcttacttt taatcatttt cttttattct     1380
ccttcttccc ccccatacat catactctcc gcaatagctc tctttcttga gtgttttgtg    1440
tcttaaactc tactgtccca ctttccgctt aatacttacc cctcctcctt ttacacattc    1500
accatg                                                              1506
```

<210> SEQ ID NO 55
<211> LENGTH: 1171
<212> TYPE: DNA
<213> ORGANISM: Aspergillus niger

<400> SEQUENCE: 55

```
tagtccaccg aggacatcga caatgccatt gtgtcggcgt ggaccagaac aacaacaact      60
ggatgaaggt gtgatggatt ggacgcttgt gtacattaat cactcaataa ccagtcattc     120
ctttgaccag atctggtaga aagacagaat tcggctgaaa ccttctctga atgtagtcca     180
tcgcgtagca ctattatgtc ccacttgctc taccatcatc gctaattctt gggattgatc     240
gtctcacttc cccatggaat atatactacc tggctcattt gatgagcccc actcctgttc     300
ttgatatata ccatgtaact tccaaattct gacggcgtag attctcctag actatttgaa     360
gtaaaataat agccatatgc tcacaaatcc aggcaacaat atcagatcat ggcaatagca     420
```

-continued

```
tcattcaggc tgatgtatta cgccaattag tagtggtagt agtagtagta gtagtagtag      480
tagtagtagt agtagtagta gcacgcatct tcaatatcaa ataaataag ctcattcttt       540
ttggtgtcca ctataaagcg atagtactgt atcgaacctc caacacagat ctatagcacg      600
acctccccgc gattgaaaat atatacatga cacaccagtc atgaccccaa gtaaaatacc      660
actgctcgca gtaggaacta aatcttcctt acctgccccc catctactcc ttccacgcgc      720
acatcatgac tactaatatc cccctcagac cccaaatcac tctcacttct ctcaacttcc      780
atcccctcac cctgaaccac tttcggcctg cacggaaaac aatcaatcag catatcccac      840
taacccccat cccccgagc aagcagaata ccaacatacc ttttctcccc ctcccaaatc       900
tgcaacctcc acgtcgccac cgtcgaaata atcaaaatca cagacataat cgtcaccgta      960
ataaacccct ccggtactgc ggtgcatcca cctgctgcca caccaccagc ggcaaccagg     1020
cttgaaacac gtacgccatt tcgttcatgc tgcccacgac tagcgcgcgc tcttcgttgt     1080
catcggtgca gatctcgtgg gcccatcttt acattttatt aggttagttt cggggatgg      1140
agggatggga tgggggagg gggttggcac c                                     1171
```

<210> SEQ ID NO 56
<211> LENGTH: 878
<212> TYPE: DNA
<213> ORGANISM: Aspergillus niger

<400> SEQUENCE: 56

```
taagatgaga cttggcgtgt gaatatactg cgaatgatgt tcgatttctt gtgattatgt       60
ttgggttcgg cgctggacga cgtatggata tggacatgga catggatatg agtttgattt      120
gattgagcgt gtacattact tcactgggta tgcttctgga atgttacctt gtcgatctct      180
tatttcatac tcctccatct ggggtttacc gacacccggt attcccaatc aaaactaact      240
gcagttcaca ccgatcgaca ctactgaatt gcatcgcacc tcgttccaag gatatcctcg      300
cttccagaga aacaaactac gccctcgcag ctctaacctc tcttggcacg cccgtattga      360
ctggccgacc agcaggcgaa ggcttggccg tatatatact ttatccggtc ctcggcctcc      420
gacccactgc ttgcctctat ccggatataa gcatccactt caccaagacg ctatccgcca      480
ctacagcatg ctttgggata atgtcccact caattgccac tcctactcac cgtataggtc      540
ttcttcgctt ggctgaagat ataagtttcc aggcaactat acttggctga tcttggcatg      600
ttcgaggaag atggaagggg cataggttac ggggttactg agtaacgggt ggaaaggagg      660
gagaattggg ttgttgttta aatgtctggt gggagccggg gggtgttgaa gttggaattt      720
gatcgttata gtcgcccgtt tgatactagt cgctctttta tacgttcact ttgtttgttg      780
gctaccatga agctgtctct ggctgttggg gcagccctga tgggatctgc tctggcagtg      840
gatattgatc ccatcgtcat caaggtagac cagctcag                             878
```

<210> SEQ ID NO 57
<211> LENGTH: 1150
<212> TYPE: DNA
<213> ORGANISM: Aspergillus niger

<400> SEQUENCE: 57

```
taatgcctta ttttgatctt tcttctttag cacggctcat ctacggttga gtggcctgca       60
tggcgttggg acggttgttt tcatcggttt ttatgatacg gataaattgg gcatacctta      120
gggtcaccat cttccatggt gccttgcgtc attctttac ctaggaatca attcaataat       180
```

-continued

```
catattccac ctgatatcta ccgcttttt tttgtagatt tagtaggaac ttgaggtaga      240
ccgttacacg ctttcagaga cgccgtcaac gtgcagttca agtcgctatc aaccaccta      300 cataacaaca tgagacgata tcaaatagga actgaatagc ttcaacttca tctacctgta    360
aattatcgaa caagtaacag acatcgagcg tgagtcaccg tcttcgccac ccgtatctcg    420
gcacgtgact gataccgtcc caaggcggcg tgggacagga agtagcttc cattcatgaa      480 gctgacccag gagagcagtt gcaggcctgt agcacgctgg agatgtgagc atcagtcgtg    540
atgccctcct acttctacca cattgcgatc gaattatttg ctcgcccgca ctctgacctc    600
caaggcacat acccaggcgt ggacaagcac tcgacgtcgc tatctttcga ctccgcatgc    660
gaatctctac tcccgttcca gaagcgccgg cactcaccgt gggcacatcg atcttctcgt    720
catcaagcgc atgggaaaca cccacgcccc tcacccaaca ctttcgccga aacccacggc    780
tcagactcta caaccagcgt tgcggacctc cgtaccctc acctctacac gacttcgccg     840
acaagcgcat ccgacttcga gcgcgacctc aggcttgata agtatccat cgagtgcatt     900 gacatgatcc catcggagca ggacacaact gctgcgaagc ggacgggctg aagaatgca     960 aaggagaatc ccatcgcgac cgggatcggc acggatatct tgggaggact acgcacgaaa    1020
ggcaaataca taccgctaga ccagagtacg tcggagagtg tttggggaat cgtgcatctt    1080
taccgagatg ctcaggagac gccgttcttg acagaagagg actacccctc gtacttgaaa    1140
ggttcggcag                                                            1150

<210> SEQ ID NO 58
<211> LENGTH: 938
<212> TYPE: DNA
<213> ORGANISM: Aspergillus niger

<400> SEQUENCE: 58
tagaacaacc aactaccttt ggattccatt agatctgctt taccttggac ttttatcccg      60
tgataccttt ttgtgctgtt ttttattcta ttccattcta ccatccatct ctcacctaag    120
agggaaagag agacggacaa ccccatttta cccacccact ttactttcca atatattaca    180
attccaattt gaatcaaatt caaatccaaa tctaaattaa attaaattaa acacaacaca    240
tcacaaactt cctacacaaa aattgtaata atcaaatcat aaatcacatt caccaaacct    300
gaccctctcc acaagtccac atactaatct ttcccccta aacacactat tgggcccgt      360 tccacggatc ccccgaccca gaaagcagca acattggtcc ttgctcctcc ttaccccgtt    420
gacttctaca tatccatgga caacacacag cacctgccgt gttcattggc cggaaggcta    480
ttttggggtt tccatcgtct ggttttgttc atgttgatta tcatggagat ttaccgggtt    540
gggtttggtc tgggctcgct tggctgcggg tttctttttt ctttttcttt tttcgtgag     600 gagttgagga cgtgttttaa gtaatttctt gattgagagt gagagagata agtactagtg    660
gggttcggct tggttccaat ggctcggtaa attgggcctt cgtcagtgag tgactctacg    720
tagtagataa tgtagagtct ggagagtctg gatttttttcc tcgcgtttct tggctggctt    780
ggcttgtgta acgtcagtt gactagtact ttttgttgtt tcttgcttgg ggttgttaga     840
cgaggtctag atagaagtag agattcagag gtaaaagact gttaagcggg tatgtatcat    900
gacaggtgtt taggttaggt aggtagtagt cggtggat                             938

<210> SEQ ID NO 59
<211> LENGTH: 423
<212> TYPE: DNA
<213> ORGANISM: Aspergillus niger
```

<400> SEQUENCE: 59

```
tagaggggag attaaaggag agtgcactgt ggagtagatg ggcactcttg atgaaactgt        60
ctataatatt attgttagta gatggtgatg atggtatata tgctctcatc tctgtatatg       120
tctgtgatgg tgtcattatc atgtatggta cgacatggat gtgattttaa tgttaatgct       180
atgatcttct atcattattt ctaaatccac ttatatcctg tgtctacgtt atcaaccgtt       240
ctccactcat ttcccctctt atttgccact accggcttct tgccattcca cttgctgaat       300
cgccctagcc cgcgcttgag cagagccagc actgacatca ttgctctgta cagaggcctg       360
cccccagtca tcctcgaacc gaatatccgc cacagtctta gccgcatcat ccacctcaac       420
cag                                                                    423
```

<210> SEQ ID NO 60
<211> LENGTH: 635
<212> TYPE: DNA
<213> ORGANISM: Aspergillus niger

<400> SEQUENCE: 60

```
tagacaccca cctagtaatg cttagccatc atgctaggcg ttgatcacac tttacccatt        60
gtcagccaac tacagccact ctttgaatat cagtgactac cattcgtatc accattcttc       120
tcatatctct ctcattgtat atcactatca cttcgtatac cacacatccg tagatatcta       180
tgcgtcttcc ccaaatccga ataagcattc aacgccaact gccctcccaa atgcgcaaac       240
agaatattcc cctgaatctc ccccctcttg accaaatcca tcatccccgc aaaactcttc       300
ccctcataca ccggatccgt aataaacgcc tccgcttcgc cgcaaactca atcgcctccc       360
acgtcctctt atccggcact ccatacacac ccccatgcca ctcctcccac aactccacat       420
cctcctccga tacctcctcc ctccccaacc caatcctctc cgccgtctcc ttcgcaatcc       480
gcaacacctg ctccctcgtc tcctttccgt ggcactcgca tcaatcccca ccaccctcgt       540
cttccccctc ccatttccag cctctcgatc caacttctcc aacaacttac cagcccgggc       600
cgtcgaccac gcgtgcccta tagtgagtcg tatta                                  635
```

<210> SEQ ID NO 61
<211> LENGTH: 800
<212> TYPE: DNA
<213> ORGANISM: Aspergillus niger

<400> SEQUENCE: 61

```
tgaattatga gcatatgatg gacttgcttt cgaccttgct tctttggaca tgaccggttg        60
cttagacggt ttaactagat tcccttcagc atgcgcattg tttatttgtg gttcgcctta       120
atagagcttg ggggcagcgg aatgctccta ccaatttccg ggtctgcttt tctcctttac       180
attggttctt aatgtttcat acgttgttca tgtatcctcc tagggaggag accttctctt       240
gtccagacag gagctggaat gcaattatat aagacgatga ccaataattc cagactcatc       300
aagagtcaga aagaagagtc atgaaaggac aatgattata atatggctaa tcaagatgta       360
taacttgaat aactgtctgt agtctttctc tgttttctcg accggattgt tggttgctta       420
ctgtagcata ccttgtcatg tgacatgggt gcaaagagtg gcgtgttctt cctgcaacctt      480
caccccgttg caagttgcac tggttgaccc aagcgcctaa gtgacaggaa aatggatagg       540
tagacatcct gctaggttca ggacttatc ggtgggcgtg aaaccaggca tgaccaagaa        600
tagcagcagt ttgagctaca aggacgctct attgttttac ttcacgccga ctccgtttag       660
```

```
agtatctgtc  agtctctgtc  tgacccatct  acagccaaac  ctcgtcacac  aataagcact      720
caagttcatc  taagatgact  gtgattggtc  cagaccagcc  cgggccgtcg  accacgcgtg      780
ccctatagtg  agacgtatta                                                     800
```

US 7,449,569 B2

ISOLATED FUNGAL PROMOTERS AND GENE TRANSCRIPTION TERMINATORS AND METHODS OF PROTEIN AND CHEMICAL PRODUCTION IN A FUNGUS

STATEMENT REGARDING FEDERALLY SPONSORED RESEARCH OR DEVELOPMENT

This invention was made with Government support under contract DE-AC0676RLO-1830, awarded by the U.S. Department of Energy. The Government has certain rights in this invention.

TECHNICAL FIELD

The invention pertains to isolated polynucleotide molecules of gene regulatory elements in filamentous fungi. More specifically, the present invention relates to isolation of filamentous fungal promoters and gene transcription terminators, construction of recombinant polynucleotide constructs, and methods for protein and chemical production in a fungus.

BACKGROUND

Fungi are increasingly important in the production of many commercially-useful products. For example, filamentous fungi currently produce a number of metabolites on the industrial scale including antibiotics such as penicillins and cephalosporins, and organic acids such as citric and fumaric acids. Filamentous fungi are also used for the industrial production of enzymes such as proteases and lipases.

Utilization of a filamentous fungus species for production of a desired compound often involves growing submerged cultures of the fungus. Filamentous fungi can exhibit numerous morphologies in submerged cultures, including pelleted and "filamented" morphologies. When fungi in culture exhibit a filamented morphology, the presence of the filaments can increase the viscosity of the culture medium. The increased viscosity can affect the mass transfer and aeration properties of the culture, cause mixing problems in a bioreactor, and result in decreased productivity.

Alternatively, filamentous fungi can exhibit a pelleted morphology. In contrast to cultures of fungi exhibiting a filamented morphology, fungi cultures exhibiting a pelleted morphology can have relatively low viscosities and require substantially less power for mixing and aeration of the culture. Productivity for many compounds, for example citric acid, itaconic acid, statins, penicillins, and various enzymes, can be enhanced by utilizing fungus exhibiting a pelleted morphology. However, in certain fungal species, production of chemicals, for example peptic enzymes or fumaric acid, can be enhanced by utilizing a fungus exhibiting a filamented morphology. Typical practices in fungus-assisted chemical/protein production do not deliberately control the morphology of the fungus.

During fungal-morphology formation, a series of genes are up regulated or down regulated. To achieve optimal production of chemicals and/or proteins of interest, one can utilize the promoters and transcription terminators that exhibit strong constitutive expression of those genes. Concurrently, one can utilize induced gene expression at specific culture conditions and key stages in the cell's development to maximize gene expression and minimize adverse effects on fungal growth that may be associated with the enhanced production of certain chemicals and/or proteins. Thus a need exists for isolated fungal promoters and transcription terminators for regulation of gene expression in a fungus as well as methods for promoting enhanced production of desired chemicals and proteins.

SUMMARY

In view of the foregoing and other problems, disadvantages, and drawbacks of traditional chemical and protein production in a fungus, the present invention has been devised. The invention encompasses isolated polynucleotide molecules comprising polynucleotide sequences that regulate the expression of genes that are differentially expressed in a native fungus exhibiting a pelleted morphology relative to a filamented morphology. In one aspect, the invention encompasses promoters that possess strong, constitutive activity in genes that are differentially expressed in native fungi exhibiting a pelleted morphology relative to a filamented morphology. The invention also encompasses inducible gene promoters that, for example, initiate expression at certain developmental stages in the native fungus. In another aspect, the invention encompasses transcription terminators from genes that are differentially expressed in native fungi exhibiting the pelleted morphology relative to native fungi exhibiting the filamented morphology.

One object of the present invention is to introduce new genetic material into eukaryotic organisms such as filamentous fungi to establish new strains for use in production of chemicals and/or proteins.

Another object of the present invention is to regulate the morphology formation in filamentous fungi.

A further object of the present invention encompasses a method for constitutive production of a compound, such as in chemical and protein production utilizing a transformed host cell.

A still further object of the present invention encompasses a method of induced production of a compound from a transformed host cell.

Another object of the present invention is to use the isolated *Aspergillus niger* (*A. niger*) promoters to regulate expression of foreign genes as well as reintroduced native genes for chemical or protein production.

DESCRIPTION OF DRAWINGS

Preferred embodiments of the invention are described below with reference to the following accompanying drawings.

DETAILED DESCRIPTION

Figure 1:
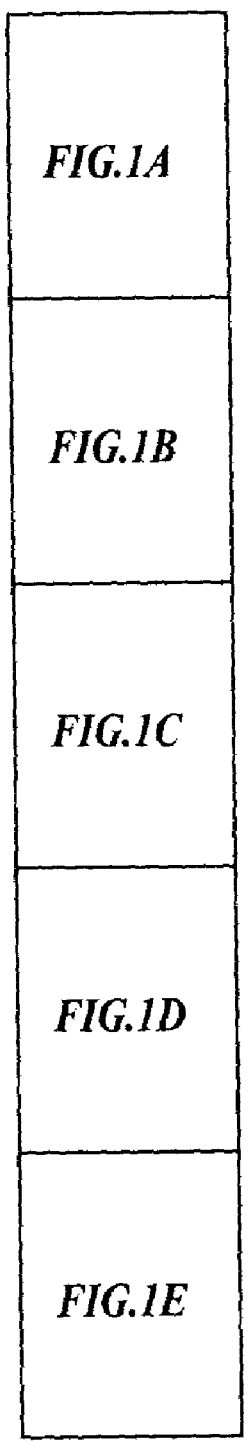
FIGS. 1A-1E compare the isolated nucleotide sequences for the promoter region of the *A. niger* Balu-42 gene, SEQ ID NO:50 (top sequence), and for the promoter region of the *Aspergillus kawachii* cwpB gene for a hypothetical protein.

For a clear and concise understanding of the specification and claims, including the scope given to such terms, the following definitions are provided:

The filamentous fungi of the present invention are eukaryotic microorganisms and include all filamentous forms of the subdivision Eumycotina. A vegetative mycelium composed of chitin, cellulose, and other complex polysaccharides characterizes these fungi. The filamentous fungi of the present invention are morphologically, physiologically, and genetically distinct from yeasts. Vegetative growth by filamentous fungi is by hyphal elongation while carbon catabolism is obligately aerobic. Various species of filamentous fungi from the three major fungal groups may be used as expression hosts including Basidiomycetes, Ascomycetes, and Zygomycetes. An exemplary member of the Basidiomycetes group is *Phanerochaete chrysosporium*. Exemplary members of the group of Ascomycetes and Imperfect Fungus include *Aspergillus niger, Aspergillus oryzae, Aspergillus terreus, Emericella nidulans, Neurospora crassa, Fusarium oxysporum, Penicillium chrysogenum*, and *Trichoderma reesei*. Exemplary members of the Zygomycetes group include but are not limited to *Rhizomucor miehei* and *Rhizopus oryzae*.

As used herein, the terms filamented and pelleted can refer to the morphology of filamentous fungi. Thus, filamentous fungi can be characterized by having a filamented morphology or a pelleted morphology.

As used herein, a morphology-enhanced promoter can refer to a DNA sequence that, when operably linked to a gene, can exhibit enhanced promoter activity and increased transcription of that gene in a specific morphology compared to some or all other morphologies in an organism. For example, a pelleted-enhanced promoter is a DNA sequence that directs a relatively higher level of transcription for genes associated with a pelleted morphology. An analogous term can be applied to transcription terminators.

A cloning vector is a DNA molecule, such as a plasmid, cosmid, or bacteriophage, which has the capability of replicating autonomously in a host cell. Cloning vectors typically contain one or a small number of restriction endonuclease recognition sites at which foreign DNA sequences and marker genes can be inserted in a determinable fashion without loss of an essential biological function of the vector. The marker gene aids in the identification and selection of cells transformed with the cloning vector. Marker genes can typically include genes that provide tetracycline, kanamycin, or ampicillin resistance.

A transgene expression vector can mean a DNA molecule comprising a foreign gene that the host cell expresses. Typically, certain regulatory elements, which include constitutive or inducible promoters, morphology-specific regulatory elements and enhancers, and transcription terminators control expression of the gene. Such a gene is said to be "operably linked to" the regulatory elements.

A recombinant host can be any prokaryotic or eukaryotic cell that contains one or more recombinant DNA molecules, whether or not the DNA is genomically integrated. This term also includes those prokaryotic or eukaryotic cells that have been genetically engineered to contain the cloned gene(s) in the chromosome or genome of the host cell.

A transgenic fungal strain is a fungal strain having one or more fungal cells that contain a foreign gene. In eukaryotes, RNA polymerase II catalyzes the transcription of a structural gene to produce mRNA. A DNA molecule can be designed to contain an RNA polymerase II template in which the RNA transcript has a sequence that is complementary to that of a specific mRNA.

Constitutive can refer to continuous expression of a gene without any regulation. When used in conjunction with a particular morphology, it can also refer to expression of a gene under all conditions for that morphology.

Homology can refer to the degree of similarity between sequences of nucleic acids or amino acids with regard to positional identity. It can also refer to the concept of similar functional properties among different nucleotide or amino acid sequences.

Foreign gene as used herein can refer to genes from other organisms as well as native genes that are re-introduced to the organism.

Heterologous can refer to aspects, for example, gene expression or proteins, that derive from or relate to different organisms.

The present invention encompasses nine promoters and seven transcription terminators discovered in a fungal strain, *Aspergillus niger (A. niger)*, which is a citric-acid-producing organism. The nucleotide sequences for the pelleted-enhanced promoters for the Arsa-7, A-37, Arsa-43, and A-90 genes as well as the filamented-enhanced promoters for the Brsa-25, Brsa-47, Brsa-109, and Brsa-118 genes are set forth in SEQ ID NOs. 46-49 and 51-54, respectively. The nucleotide sequence for the promoter for the Balu-42 gene is set forth in SEQ ID NO:50 and has a 66.9% identity to the promoter region of *Aspergillus kawachii* cwpB gene for a hypothetical protein, as shown in FIGS. 1A-1E. The length of filamented-enhanced gene promoter Balu-42 is 2271 base pairs. Based on a Basic Local Alignment Search Tool (BLAST) search, the remaining promoters show no homology to any known promoters in the GeneBank database, the European Molecular Biology Laboratory-European Bioinformatics Institute (EMBL-EBI) fungi nucleotide database, or the genome database of *A. nidulans, N. crassa*, and *M. grisea*.

The nucleotide sequences for the three filamented-enhanced transcription terminators for the Brsa-25, Brsa-47, and Brsa-118 genes, as well as the four pelleted-enhanced transcription terminators for the Arsa-7, A-37, Arsa-43, and A-90 genes are set forth in SEQ ID NOs. 59-61 and 55-58, respectively. These transcription terminators do not show any significant similarity to known sequences in the GeneBank database, the EMBL-EBI fungi nucleotide database, or the genome database of *A. nidulans, N. crassa*, and *M. grisea*. The genes associated with the 16 regulatory elements encompassed by the resent invention are described in published U.S. patent application Ser. No. 10/442,017, titled "Isolated Polynucleotides and Methods of Promoting a Morphology in a Fungus" by Lasure et al., the contents of which are herein incorporated by reference.

The actual promoter fragments and transcription terminators comprising the polynucleotide sequences set forth in SEQ ID NOs. 46-61 were obtained from *A. niger* strain number 11414 at the American Type Culture Collection (ATCC11414). Culture samples of *A. niger* (filamented morphology) were harvested two days after inducement. The samples were centrifuged to form culture pellets, which were frozen with liquid nitrogen and stored at −80° C. for total genome DNA extraction. Total genomic DNA of *A. niger* was extracted by the cetyltrimethylamrnonium bromide (CTAB) method.

Genome walking served as an effective means for isolating the desired nucleotide sequences. Briefly, the technique consists of digesting genomic DNA with restriction endonuclease Dra I, EcoR V, Puv II, or Stu I and linking the respective fragments with an adaptor oligonucleotide to form four genome walking libraries named DraI, EcoRV, PvuII, or StuI library, respectively. A gene-specific primer (GSP) and an adaptor primer provided by the manufacturer of the GENOMEWALKER™ kits (Clontech Laboratories, Inc., Palo Alto, Calif.) were used to isolate the gene-specific promoter or transcription terminator fragments. The genomic DNA sequence was determined by sequencing the DNA polymerase chain reaction (PCR) products. One GSP was designed for promoter isolation and another one for gene transcription terminator isolation.

Once identified, each of the promoters and transcription terminators described above can be operably linked to additional DNA segments to form DNA constructs. A first DNA segment comprising at least a portion of a functional promoter sequence encompassed by the present invention (SEQ ID NO:46-54) can be operably linked to a second DNA segment comprising a DNA sequence coding a protein of interest. For example, the second DNA segment may comprise a GUS reporter gene or it may comprise a coding sequence that is differentially expressed in a native fungus exhibiting a pelleted morphology relative to the native fungus exhibiting a filamented morphology. Alternatively, the second DNA segment can comprise a sequence encoding a protein of interest which is not natively expressed in fungus, or which does not exhibit morphology-based differential expression in native fungus. Specific examples of proteins of interest include, but are not limited to cellulases, amyglucosidases, amylases, lipases, microbial rennets, xylanases, galactosidases, mannanases, glucanases, phytases, monoclonal antibodies, bovin serum albumin and human blood coagulation-associated proteins. Furthermore, the 3'-end of the second DNA segment in the construct can be operably linked to a third DNA segment comprising a transcription terminator. In a preferred embodiment, the third DNA segment comprises at least a portion of a transcription terminator encompassed by the present invention (SEQ ID NO:55-61).

The present invention can also encompass a vector. A non-limiting example of such a vector can be one that will produce a fungus carrying the DNA sequence of interest, and can comprise, though at low efficiency, a naked piece of DNA capable of conferring the properties of this invention. Another example of a vector includes a transgene expression vector for the fungal strain, *Aspergillus niger*, which utilizes one of the native promoters to regulate the expression of a β-glucoronidase (GUS) reporter gene in *A. niger*. Further, this vector can be used as a chromosomal integration vector for other foreign gene expression in *A. niger*.

Additional examples of vectors can comprise the DNA construct as described above as well as lactate dehydrogenase cDNA from *Rhizopus oryzae* for lactic acid production in *Aspergillus niger*, genes of cellulases from *Trichoderma reesei*, cDNA of hen egg-white lysozyme (HEWL), and cDNA of single chain Fv (scFv) antibody fragments. The DNA fragments, which comprise the coding sequences of any of genes of interest, can be inserted between the 5'-end and the 3'-end of a promoter and a transcription terminator, respectively, of the present invention.

The constructs and vectors as described above can utilize promoter sequences of the present invention having strong, constitutive activity or inducible gene promoters that, for example, initiate expression at certain developmental stages in the native fungus. Examples of developmental stages can include, but are not limited to vegetative, sexual, pelleted morphology formation, and filamentous morphology formation. The early pelleted morphology formation stage can occur approximately 6 to 12 hrs after inoculation of spores into culture medium. Late pelleted morphology formation stage can occur, for example, 3 days after inoculation of spores into the culture medium The particular method of transformation typically guides selection of an appropriate vector, or whether to even use a vector. For example, a heterologous nucleic acid sequence can be introduced into a fungal cell utilizing *Agrobacterium tumefaciens* containing a Ti plasmid. When using an *A. tumefaciens* culture as a transformation vehicle, it can be most advantageous to use a non-oncogenic strain of the *Agrobacterium* as the vector carrier so that normal non-oncogenic differentiation of the transformed cells is possible. It can also be preferable to have the *Agrobacterium* harbor a binary Ti plasmid system. The binary system comprises 1) a first Ti plasmid having a virulence region that is essential for the introduction of transfer-DNA (T-DNA) into fungi, and 2) a chimeric plasmid. The chimeric plasmid contains at least one border region of the T-DNA region of a wild-type Ti plasmid flanking the nucleic acid to be transferred. Binary Ti plasmid systems have proven to be effective in transforming fungal cells. Such a binary system can be preferred because it typically does not require integration into the Ti plasmid in *Agrobacterium*.

Methods involving the use of *Agrobacterium* include, but are not limited to :1) co-cultivation of *Agrobacterium* with fungal spores; 2) transformation of fungal cells or tissues with *Agrobacterium*; and 3) transformation of fungal protoplasts with *Agrobacterium*.

The construct described herein can also be introduced into a fungal cell chemically through contact between the cell and the construct. For example, nucleic acid may be transferred into fungal cells using polyethylene glycol/$CaCl_2$-mediated genetic material uptake by the fungal cell. Alternatively, the nucleic acid can be introduced into fungal cells by electroporation. In this technique, fungal protoplasts are electroporated in the presence of vectors or nucleic acids containing the relevant nucleic acid sequences. Electroporated fungal protoplasts can reform the cell wall, divide and form fungal tissues. Selection of the transformed fungal cells with the transformed gene can then be accomplished using phenotypic markers. The nucleic acid can also be introduced into fungal cells by microprojectile particle bombardment (biolistic) transformation. The nucleic acid can be coated on particles for nucleic acid delivery by rupture discs. The particles can comprise tungsten (M5) while the rupture discs can be, for example, 1100-psi rupture discs. The optimal distance between the rupture disc and the tungsten particle carrier and between the launch assembly and target cells can be adjusted to suit different fungal cells.

The vectors described above can be used to facilitate the expression and/or secretion of heterologous proteins in fungal fermentation culture. Fungal cells comprising a transgene expression vector that allows high-level expression of a protein product of interest can be placed and maintained into fungal fermentation cultures and induced using appropriate agents. The protein of interest can be mammalian proteins, plant proteins, fungal proteins, or bacterial proteins, including, but not limited to, human blood factor proteins, plant proteases, fungal cellulases and hemicellulases, and thermally-stable DNA polymerases of bacteria, respectively. The result can be high-level production of the desired heterologous protein. Techniques for isolating the heterologous proteins can include, but are not limited to fractional precipitation, various chromatographies, and ultracentrifugation. In some cases, the proteins produced by the transgenic fungal cells are not the desired product, but are used rather to enhance production of another chemical. In such instances, the transgenic fungal cells of the present invention can be allowed to produce proteins, for example, enzymes, that enhance production of the desired chemical. Chemicals of interest can include, but are not limited to acids and statins. Examples of acids can include aconitic acid, citric acid, fumaric acid, itaconic acid, malic acid, succinic acid, oxalic acid, gluconic acid, and lactic acid. Examples of statins can include lovastatin and compactin By combining the technology of the present invention with production methods described herein as well as those that are well-established (e.g., fungal fermentation and product recovery), chemical compounds and recombinant proteins can be efficiently and economically produced for the biopharmaceutical, industrial processing, animal health, and bioremediation industries. The following examples are given to illustrate the present invention. It should be understood that the invention is not to be limited to the specific conditions or details described in these examples.

EXAMPLE 1

Isolation of Fungal Promoters and Transcription Terminators

Figure 2:
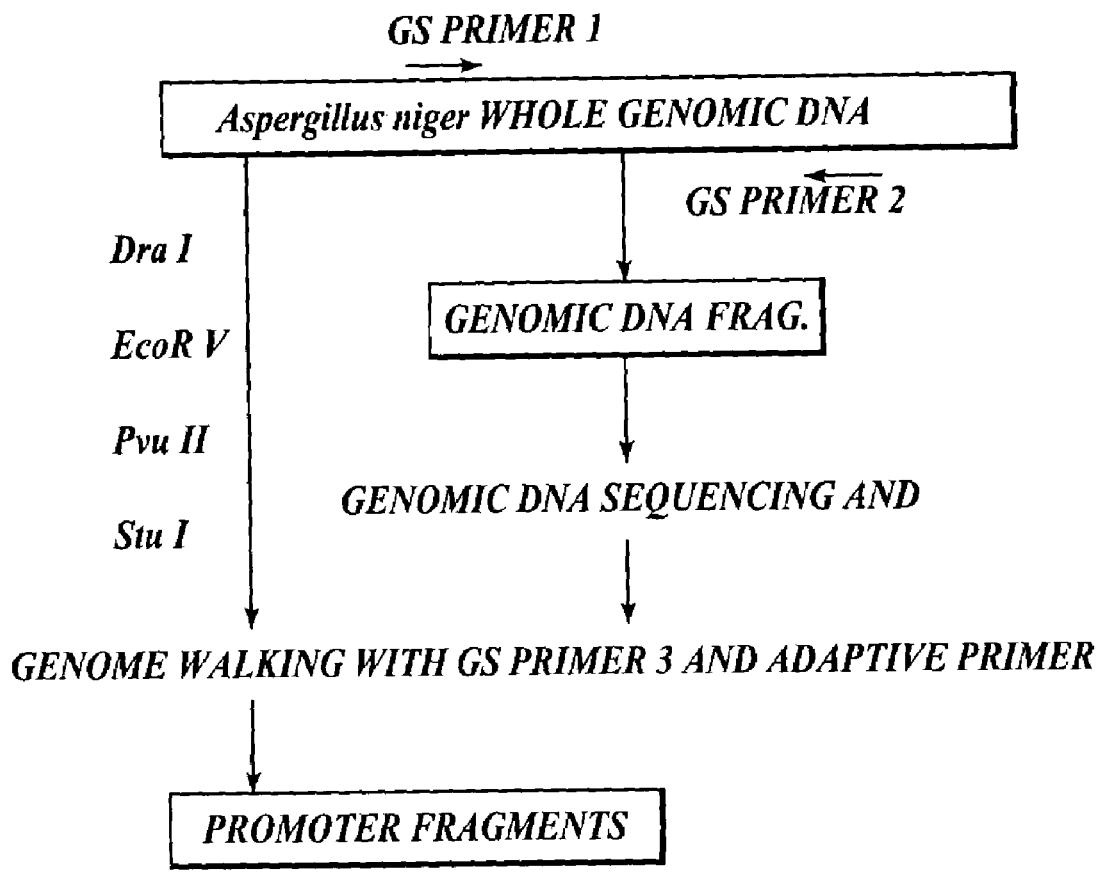
FIG. 2 is an illustration of the procedure for promoter and transcription terminator sequence isolation by genome walking.

The *A. niger* (ATCC11414) cells were grown in a liquid flask culture with non-citric acid production media containing 1000 ppb $Mn^{2+}$, 140 g/l glucose, 3.1 g/l $NH_4NO_3$, 0.15 g/l $KH_2PO_4$, 0.15 g/l NaCl, 2.2 g/l $MgSO_4.7H_2O$, 6.6 mg/l $ZnSO_4.7H_2O$, and 0.1 mg/l $FeCl_3$ adjusted to pH 2.0 with 4 M $H_2SO_4$. The biomass was then harvested by centrifugation and the genomic DNA was isolated by the CTAB method. Based on cDNA sequences of *A. niger* genes identified in U.S. patent application Ser. No. 10/442,017, two sets of gene-specific primers, GSP-1 (SEQ. ID NO.:1-9) and GSP-2 (SEQ. ID NO.:10-18) at 5'-end and 3'-end, respectively, were designed, synthesized, and used to isolate genomic DNA fragments of a specific gene by genomic PCR. The DNA sequences of specific genome DNA fragments were determined by conventional DNA sequencing. As shown in FIG. 2, the genomic DNA sequence was used as a source DNA sequence to design additional primers (SEQ. ID NO.:19-34), designated generally as gene specific primers-3 (GSP-3) for isolation of fungal promoters or transcription terminators via genomic PCR. Table 1 lists the sequences for each of the gene specific primers as well as the adaptor primers.

The genomic DNA was first digested separately with restriction endonucleases Dra I, EcoR V, Pvu II, or Stu I. This digestion generated a series of genomic DNA fragments with blunt ends. After generation of the blunt-end fragments, a GENOMEWALKER™ adaptor oligonucleotide of 48-base pairs was linked to the ends of genomic DNA fragments to generate four separate genome-walking libraries. The libraries were designated as Dra I, EcoR V, Pvu II, and Stu I, respectively. The genome-walking libraries were used as genomic DNA templates for genomic PCR with adaptor primer 1 (SEQ. ID NO. 35) or 2 (SEQ. ID NO.:36) and the appropriate GSP-3 fragment (SEQ ID NO:19-34). The PCR fragments were separated by low melting point agarose gel electrophoresis and isolated by gelase digestion and a microcon centrifugal device. The PCR fragment was then inserted into the pGEM-Teasy vector for DNA replication and DNA sequencing. The PCR fragments were aligned with known genome DNA sequences using the BLAST 2 program to verify the identity of the newly isolated promoter or transcription terminator fragment.

TABLE 1

Oligonucleotides (GSP-1, GSP-2, GSP-3, and adaptor primers) used for promoter and transcription terminator isolation

| SEQ ID NO: | Gene | Oligonucleotide name | Oligonucleotide |
|---|---|---|---|
| Gene specific primer (GSP-1) used for genome DNA isolation | | | |
| 1 | Balu-42 FP-35 | (Balu42-5P) | 5'-CCA CGG TAG TCA CTC CTT TGC ACT A-3' |
| 2 | Brsa-25 FP-37 | (Brsa25-5P) | 5'-CCT CTA TTC TGT CTC CCT TCG GCG AT-3' |
| 3 | Brsa-47 FP-51 | (Brs47-P5) | 5'-GCA ATC GTC TTC CCG TCG TTC A-3' |
| 4 | Brsa-109 FP-55 | (Brs109-P5) | 5'-GTC TGT CGT GGT GTC GTA TCA AAT G-3' |
| 5 | Brsa-118 FP-39 | (Brsa118-5P) | 5'-CTC CTT CTT CCC CCC CAT ACA TCA-3' |
| 6 | Arsa-7 FP-47 | (Arsa-7-P5) | 5'-GCT GTG CTT CGT ACC TTC ATT TCG-3' |
| 7 | A-37 FP-43 | (A37-5P) | 5'-GCC ATC TAT CAA CAC GAG AGA AAA C-3' |

TABLE 1-continued

Oligonucleotides (GSP-1, GSP-2, GSP-3, and adaptor primers) used for promoter and transcription terminator isolation

| SEQ ID NO: | Gene | Oligonucleotide name | Oligonucleotide |
|---|---|---|---|
| 8 | Arsa-43 | FP-95 (Arsa43-5P) | 5'-TGC AGA TCT TCG TTA AGA CCC TCA C-3' |
| 9 | A-90 | FP-57 (A90-5P) | 5'-CTC TCC CAC CTC CCC AGC CTT TCC T-3' |

Gene specific primer (GSP-2) used for genome DNA isolation

| | | | |
|---|---|---|---|
| 10 | Balu-42 | FP-36 (Balu42-3P) | 5'-GAG TCG ACG AAT CGA ATC GAA TCG-3' |
| 11 | Brsa-25 | FP-38 (Brsa25-3P) | 5'-GAC ACC ATC ACA GAC ATA TAC AGA GA-3' |
| 12 | Brsa-47 | FP-52 (Brs47-P3) | 5'-CAA AGA GTG GCT GTA GTT GGC T-3' |
| 13 | Brsa-109 | FP-56 (Brs109-P3) | 5'-GTG CCC ATC AGA AGT GAA CCA AGA-3' |
| 14 | Brsa-118 | FP-40 (Brsa118-3P) | 5'-GCA TTC CAG CTC CTG TCT GGA CAA-3' |
| 15 | Arsa-7 | FP-48 (Arsa-7-P3) | 5'-CAC AAG CGT CCA ATC CAT CAC A-3' |
| 16 | A-37 | FP-44 (A35-3P) | 5'-GAG ATC GAC AAG GTA ACA TTC CAG AA-3' |
| 17 | Arsa-43 | FP-96 (Arsa43-3P) | 5'-GCG GAG GAC AAG ATG GAG AGT AGA C-3' |
| 18 | A-90 | FP-58 (A90-3P) | 5'-CCA AGG TAA AGC AGA TCT AAT GG-3' |

Gene specific primer (GSP-3) used for promoter isolation

| | | | |
|---|---|---|---|
| 19 | Balu-42 | FP-79 (Balu-42R) | 5'-ACT TTC GTG TCT TGT GCG TGA AGT AA-3' |
| 20 | Brsa-25 | FP-81 (Brsa-25R) | 5'-GGT TTC TTT ATC CTG TCC GTA TGC TG-3' |
| 21 | Brsa-47 | FP-85 (Brsa-47R) | 5'-GAC GGT TTA TAT TCG ACC ACG CCT CA-3' |
| 22 | Brsa-109 | FP-87 (Brsa-109R) | 5'-GCT AGT GGC CTT CAT TGT TGT ATG AG-3' |
| 23 | Brsa-118 | FP-89 (Brsa-118R) | 5'-TGA ATG TGT AAA AGG AGG AGG AGG AA-3 |
| 24 | Arsa-7 | FP-91 (Arsa-7R) | 5'-AGT AAG ACG AAA TTG AGG TAC GAA GC-3' |
| 25 | A-37 | FP-93 (A-37R) | 5'-CAG CAG CAG ACA TTG TGA TGT GAT AG-2 |
| 26 | Arsa-43 | FP-99 (Arsa-43R) | 5'-GAT GCC CTC CTT ATC CTG GAT CTT G-3' |
| 27 | A-90 | FP-105 (A-90R) | 5'-GCG GTC AGA AGA GAC TTG AAG GAG AC-3' |

Gene specific primer (GSP-3) used for transcriptional terminator isolation

| | | | |
|---|---|---|---|
| 28 | Brsa-25 | FP-82 (Brsa-25L) | 5'-CTG TGG AGT AGA TGG GCA CTC TTG AT-3' |
| 29 | Brsa-47 | FP-86 (Brsa-47L) | 5'-CAC CCA CCT AGT AAT GCT TAG CCA TC-3' |
| 30 | Brsa-118 | FP-90 (Brsa-118L) | 5'-TTT GTG GTT CGC CTT AAT AGA GCT TG-3' |
| 31 | Arsa-7 | FP-92 (Arsa-7L) | 5'-ATC ATC TGA TCA CGC TGA TGC AAT AGT TC-3' |
| 32 | A-37 | FP-94 (A-37L) | 5'-GGA CAT GGA CAT GGA TAT GAG TTT GA-3' |
| 33 | Arsa-43 | FP-100 (Arsa-43L) | 5'-CTT TAG CAC GGC TCA TCT ACG GTT G-3' |
| 34 | A-90 | FP-104 (A-90L) | 5'-TTG AGC TCG AGT GGA AAG GTG TAC G-3' |
| 35 | | Adaptor primer-1 | 5'-GTA ATA CGA CTC ACT ATA GGG C-3' |
| 36 | | Adaptor primter-2 | 5'-ACT ATA GGG CAC GCG TGG T-3' |

Gene specific primer used for deletion of ATG-transcription start site at the promoter fragment's 3'-end

| | | | |
|---|---|---|---|
| 37 | Arsa-7 | FP-135 (pArsa-7-412H5) | 5'-TCA AGC TTC TGC TCC AAC GCG CTA TCA AAT CGA A-3'C-3' |
| 38 | Arsa-7 | FP-136 (pArsa-7-2040P3) | 5'-CAC AGC TGA TTG AAA GAA TAG AGA GTG ATG GAG TTG -3' |
| 39 | A-37 | FP-125 (A-37-P-XbaRI) | 5'-CGG AAT TCT CTA GAG TGA TGT GGA TAG GGA TGG GAA TAA G-3' |
| 40 | Arsa-43 | FP124 (Arsa-43-P-Cla-H3) | 5'-CCA AGC TTA TCG ATG TTG TAG AAG CGC AGT AAA TGG TGT ATG -3' |
| 41 | Brsa-25 | FP-152 (Brsa25-1677Sma) | 5'-ATC CCG GGT AAA GCA AGG CGA ATG ACG AAG ACA -3' |
| 42 | Brsa-109 | FP-137 (PBrsa-109-23S5) | 5'-CAG AGC TCC TCC TGT CTG AGT GTT GTC TCA -3' |
| 43 | Brsa-109 | FP-138 (pBrsa-109-1835P3) | 5'-CTC AGC TGT TGT ATG AGA GGT GTA TAT GTA TGT -3' |
| 44 | Brsa-118 | FP-155 (Brsal18-1502pml) | 5'-GCA CGT GAA TGT GTA AAA GGA GGA GGG GTA -3' |
| 45 | | T-7 primer | 5'-TAA TAC GAC TCA CTA TAG GG-3' |

EXAMPLE 2

This example describes the steps taken to prepare different fungal promoters fused in front of a GUS reporter gene with the 3'-TtripC transcription terminator. Use of the constructs produced according to this example demonstrates the function of different promoters and their potential use in the production of different proteins and chemicals via various fungi.

Figure 3:
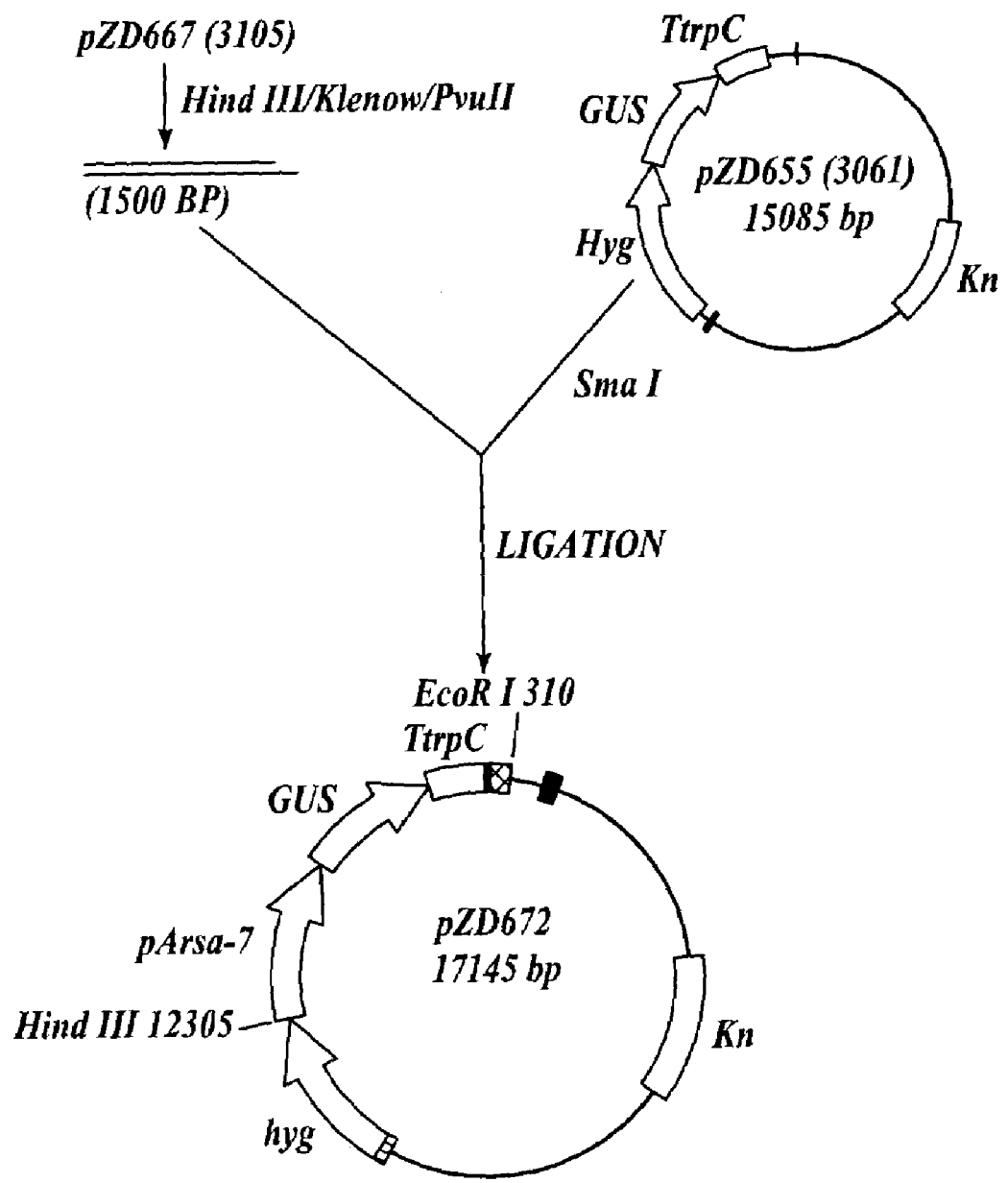
FIG. 3 is a schematic illustrating a plasmid vector pZD672, which contains the promoter region of the pelleted-associated Arsa-7 gene (SEQ ID NO:46) and the β-glucoronidase (GUS) reporter gene, for *Agrobacterium*-mediated transformation in *A. niger*.

Since the GUS reporter gene contains its own ATG-translation start site, in the transgene expression vector, introduction of a proper restriction endonuclease site at the 3'-end of the promoter was preceded by removal of the ATG-translation start site from all the promoter fragments being prepared for function analysis. PCR fragments were cloned into the pGEM-Teasy vector and the presence of the promoter fragment was confirmed by restriction endonuclease digestion. The promoter fragment released by restriction endonucleases was inserted into binary vectors pZD640 or pZD655 for *Agrobacterium*-mediated transformation. The method of construction for specific vectors for *Agrobacterium*-mediated transformation is described as follows:

The PCR fragment containing the promoter for the pelleted-associated Arsa-7 gene (SEQ ID NO:46) was first isolated via genome walking with gene specific primer FP-91 (SEQ ID NO:24) and subsequently cloned into pGEM-Teasy vector to form pZD611. The plasmid DNA was then sequenced to confirm the newly isolated fragments. In order to remove the ATG-transcription start site at the promoter fragment's 3'-end, pZD611 was used for a template for PCR with primer FP-135 (SEQ ID NO 37) and FP-136 (SEQ ID NO:38). Referring to FIG. 3, the PCR product was inserted into pGEM-Teasy to form pZD667. Then the Arsa-7 promoter fragment (SEQ ID NO:46) was excised by Hind III and Pvu II and treated with DNA polymerase I-large fragment. The promoter fragment was finally inserted into the restriction endonuclease Sma I site of pZD655 in front of GUS reporter gene to form pZD672.

Figure 4:
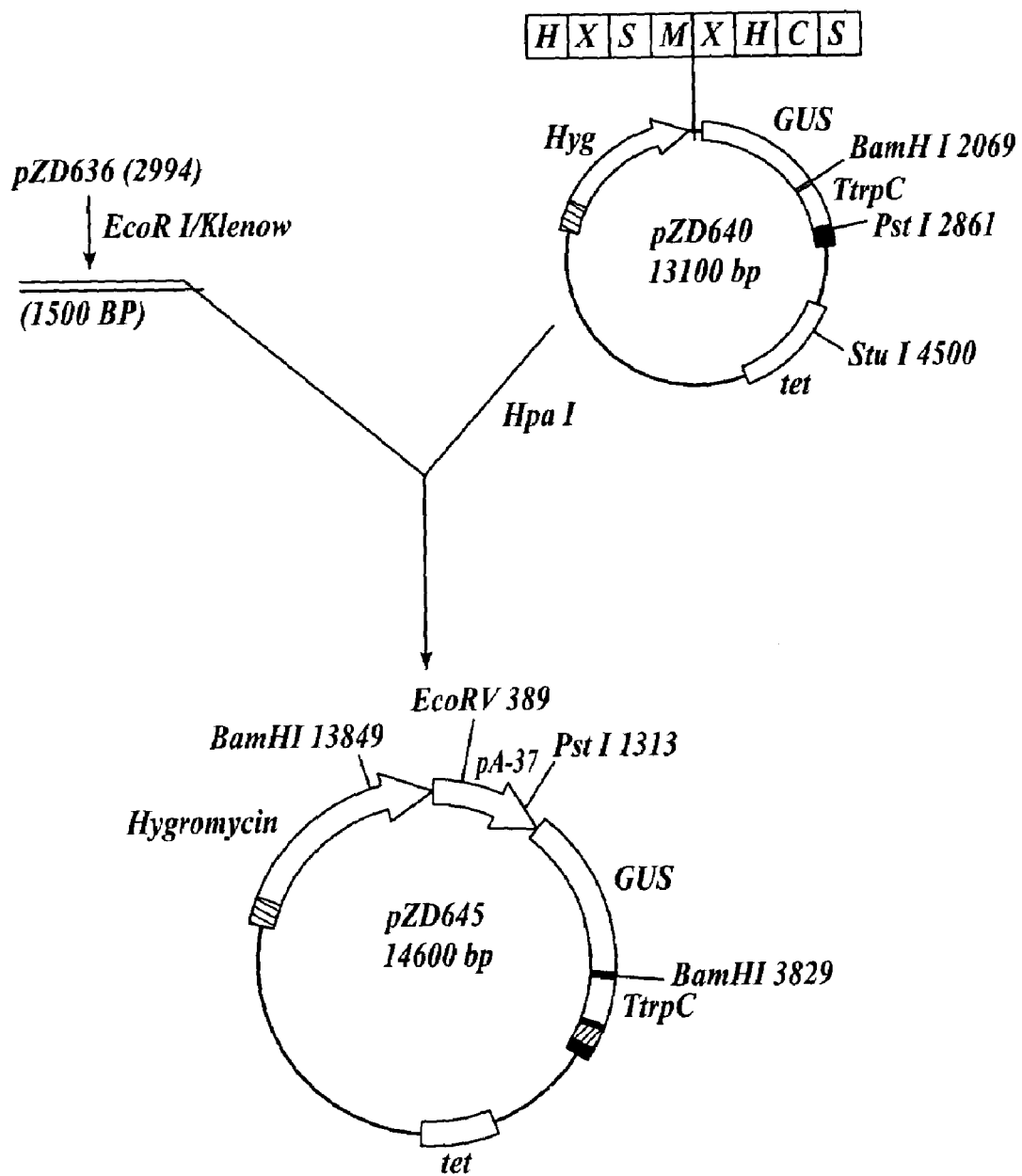
FIG. 4 is a schematic illustrating a plasmid vector pZD645, which contains the promoter region of the pelleted-associated A-37 gene (SEQ ID NO:47) and the GUS reporter gene, for *Agrobacterium*-mediated transformation in *A. niger*.

Similarly, the pelleted-enhanced A-37 gene promoter (SEQ ID NO:47) was first isolated from the genomic DNA using GENOMEWALKER™ kits and gene-specific primer FP-93 (SEQ ID NO:25), which was inserted into pGEM-Teasy to form pZD612. The A-37 promoter fragment (SEQ ID NO:47) was then prepared by PCR with primer FP-125 (SEQ ID NO:39) and T-7 (SEQ ID NO:45) and inserted into a PCR 4 TOPO™ vector (Invitrogen Corporation, Carlsbad, Calif.) to form pZD636. Referring to FIG. 4, the promoter fragment in pZD636 was excised with restriction endonuclease EcoR I and treated with DNA polymerase I-large fragment. Finally, the promoter fragment was inserted into pZD640 to form pZD645.

Figure 5:
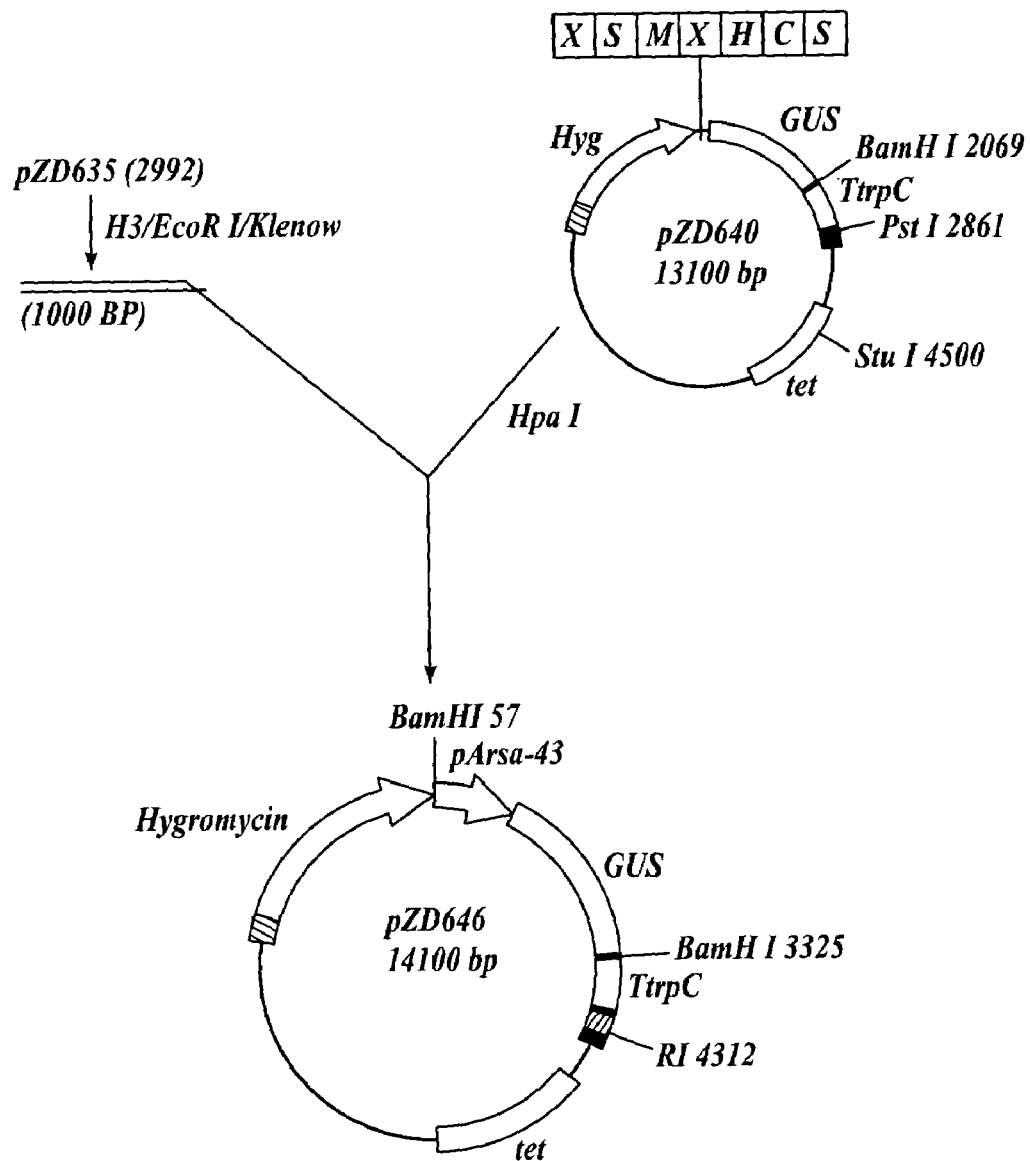
FIG. 5 is a schematic illustrating a plasmid vector pZD646, which contains the promoter region of the pelleted-associated Arsa-43 gene (SEQ ID NO:48) and the GUS reporter gene, for *Agrobacterium*-mediated transformation in *A. niger*.

The pelleted-enhanced Arsa-43 gene promoter (SEQ ID NO:48) was first isolated from the genomic DNA using GENOMEWALKER™ kits and gene specific primer FP-99 (SEQ ID NO:26). The promoter was subsequently inserted into pGEM-Teasy vector to form pZD614. The ATG-sequence at the 3'-end of the Arsa-43 promoter fragment (SEQ ID NO:48) was then removed by PCR using FP-124 (SEQ ID NO:40) and reverse primers. Referring to FIG. 5, the remaining fragment was cloned into the PCR-4-TOPO™ vector to generate pZD635. The Arsa-43 promoter (SEQ ID NO:48) was excised with restriction endonuclease Hind III and EcoR I, which was treated with DNA polymerase I, large fragment. Finally, the fragment was inserted in front of the GUS reporter gene at restriction endonuclease Hpa I site to form pZD646.

Figure 6:
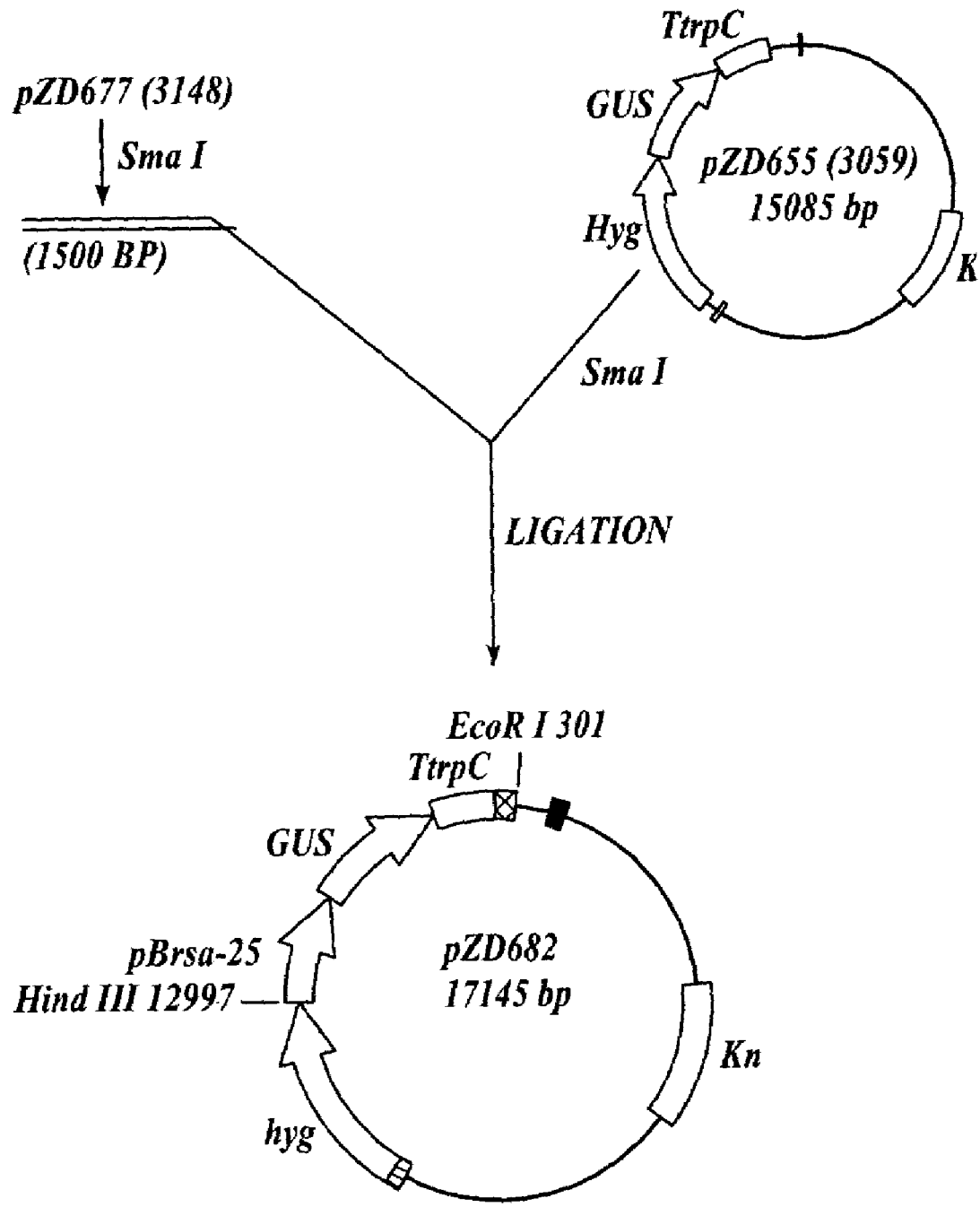
FIG. 6 is a schematic illustrating a plasmid vector pZD682, which contains the promoter region of the filamented-associated Brsa-25 gene (SEQ ID NO:51) and the GUS reporter gene, for *Agrobacterium*-mediated transformation in *A. niger*.

The filamented-enhanced Brsa-25 gene promoter (SEQ ID NO:51) was isolated using GENOMEWALKER™ kits and gene specific primer FP-81 (SEQ ID NO: 20). The isolated Brsa-25 promoter was then cloned into pGEM-Teasy vector to form pZD619. The promoter DNA fragment was confirmed by DNA sequencing. The ATG-sequence at the 3'-end of the promoter was removed and a restriction endonuclease site Sma I was added to the same end by PCR using gene specific primer FP-152 (SEQ ID NO:41) and a T-7 (SEQ ID NO:45) primer, which was further cloned into a pGEM-Teasy vector to form pZD677. Referring to FIG. 6, the promoter fragment was excised with restriction endonuclease Sma I and cloned into pZD655 to form pZD682.

Figure 7:
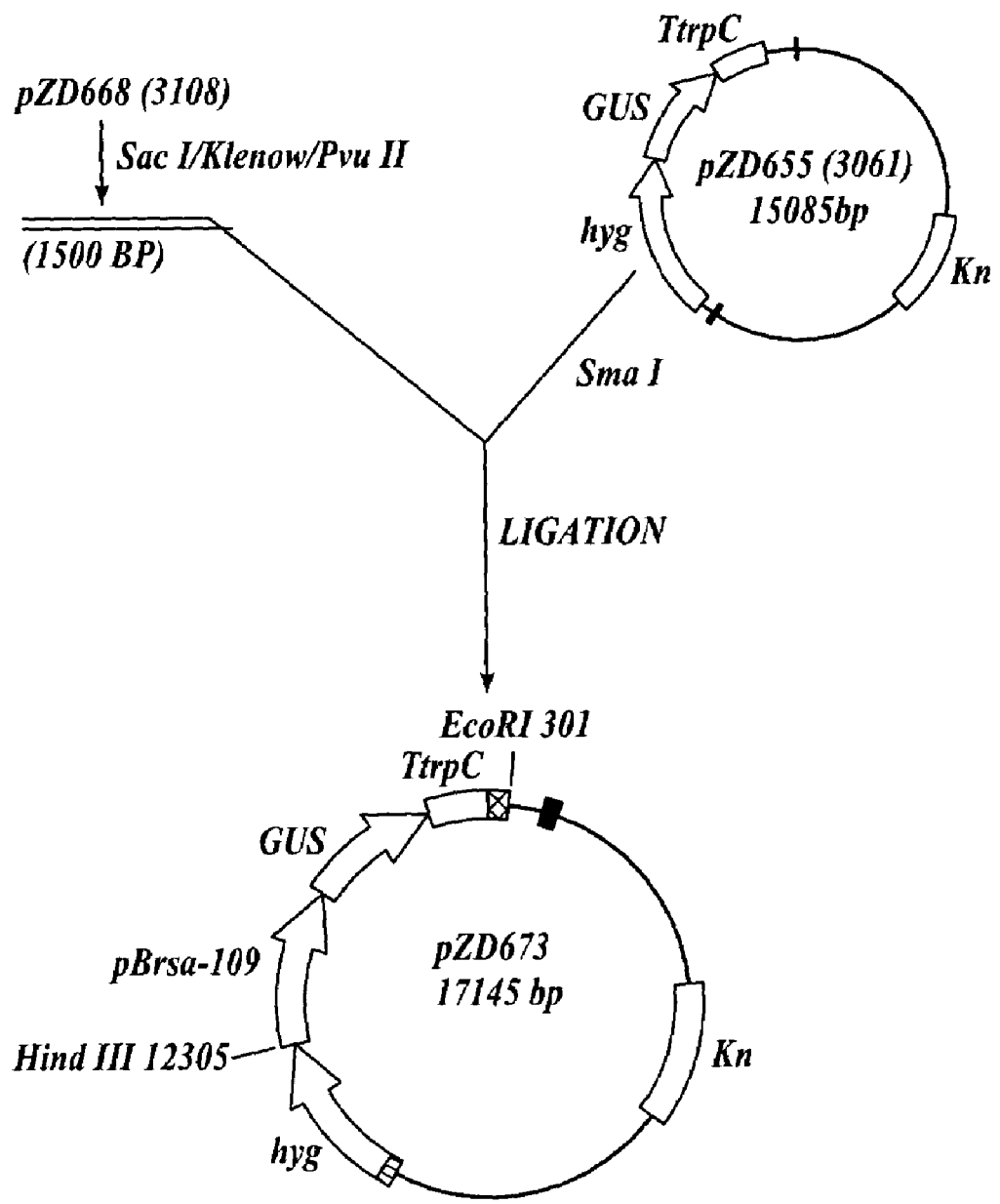
FIG. 7 is a schematic illustrating a plasmid vector pZD673, which contains the promoter region of the filamented-associated Brsa-109 gene (SEQ ID NO:53) and the GUS reporter gene, for *Agrobacterium*-mediated transformation in *A. niger*.

The filamented-enhanced, Brsa-109 gene promoter (SEQ ID NO:53) was isolated with GENOMEWALKER™ kits and gene specific primer FP-87 (SEQ ID NO: 22). The isolated Brsa-109 promoter was subsequently cloned into pGEM-Teasy vector to form pZD613. The ATG at the 3'-end of the promoter was removed and the restriction endonuclease Pvu II was introduced at the same end of the promoter fragment by PCR with gene specific primers FP-137 (SEQ ID NO:42) and FP-138 (SEQ ID NO:43). The promoter fragment was then inserted into pGEM-Teasy vector to form pZD668. Referring to FIG. 7, the promoter was isolated with Sac I and Pvu II, treated with DNA polymerase I-large fragment, and cloned into pZD655 in front of the GUS reporter gene to form pZD673.

Figure 8:
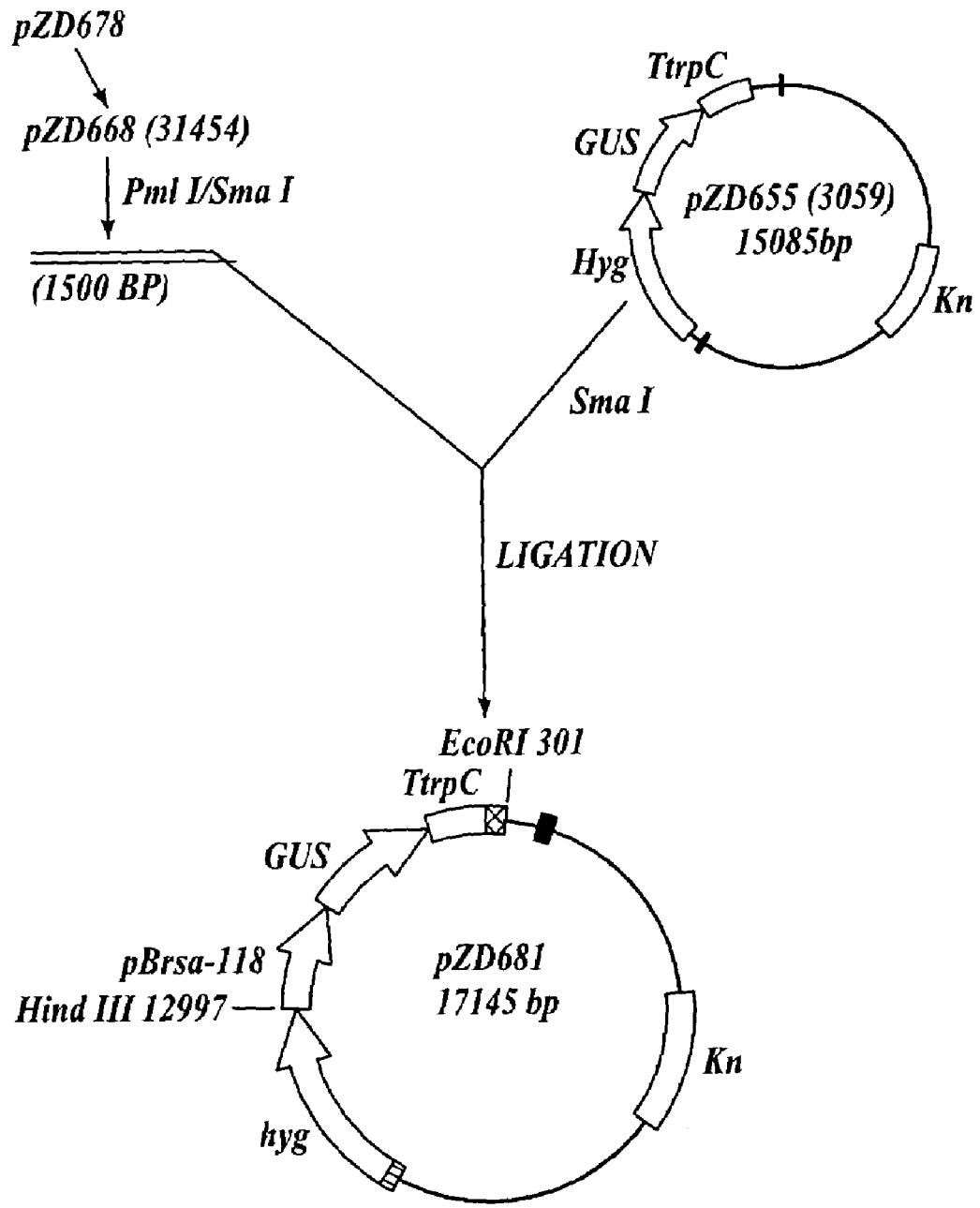
FIG. 8 is a schematic illustrating a plasmid vector pZD681, which contains the promoter region of the filamented-associated Brsa-118 gene (SEQ ID NO:54) and the GUS reporter gene, for *Agrobacterium*-mediated transformation in *A. niger*.

The filamented-enhanced Brsa-118 gene promoter (SEQ ID NO:54) was isolated with GENOMEWALKER™ kits and gene specific primer FP-89 (SEQ ID NO: 23). The isolated Brsa-118 promoter was subsequently cloned into a PCR-4-Blunt-TOPO™ vector to form pZD610. The ATG at the 3'-end of the promoter was removed and the restriction endonuclease Pml I was introduced at the same end of the promoter by PCR with gene specific primer FP-155 (SEQ ID NO:44) and T-7 primer (SEQ ID NO: 45). The promoter fragment was inserted into pGEM-Teasy vector to form pZD678. Referring to FIG. 8, the promoter was isolated out with Pml I and Sma I and cloned into pZD655 in front of the GUS reporter gene to form pZD681.

EXAMPLE 3

This example describes the methodology used for *Agrobacterium*-mediated transformation and colorimetric GUS assays of the GUS reporter gene under the control of the different *A. niger* gene promoters. Application of this system enables one to study the function of the sequences inserted in front of the reporter gene in terms of transcriptional activity.

*Escherichia coli* DH5α was used as the recombinant host for routine cloning experiments. The *Agrobacterium tumefaciens* strain AGL0 served as the host for the binary vectors and in the transformation of *A. niger.*

Transformation of the constructs carrying backbone binary vector pZD640 or 655 into *Agrobacterium tumefaciens* strain AGL0 was conducted by the freeze-and-thaw method as described by Ebert et al. in the *Proceedings of the National Academy of Sciences USA,* 84:5745-5749 (1987), the content of which is incorporated herein by reference. Plasmid DNA from the transformed *Agrobacterium* clones was isolated and digested with various restriction endonucleases and analyzed in agarose gel electrophoresis to confirm transformation of each construct. Fungal spore transformation was performed as described in the article by Dai et al., titled Identification of genes associated with morphology in *Aspergillus niger* by using suppression subtractive hybridization (Applied Environmental Microbiology 70: 2474-2485 (2004)), the content of which is incorporated herein by reference. At least 30 independently transformed fungal strains were selected for each promoter construct described in Example 2. Transformed colonies were removed from the agar selective media, which contained minimal medium (see J. W. Bennett and L. L. Lasure eds., *More Gene Manipulations in Fungi,* Academic Press Inc, San Diego, pp 441-458.) with 200 μg ml$^{-1}$ hygromycin and 200 μg ml$^{-1}$ cefotaxime, and then grown under sterile but equivalent conditions for spore production.

The spores were enumerated and then cultured in a proper culture medium at a temperature of 30° C. and a mixing speed of 250 rpm for 2 days. Finally, the biomass was harvested for a GUS activity assay. Fluorometric quantitation of GUS activity was performed according to Jefferson et al. in the *European Molecular Biology Organization Journal*, 6:3901-3907 (1987), the content of which is herein incorporated by reference.

Biomasses of independent transgenic fungal strains were harvested from fresh test-tube cultures by centrifugation at various times ranging between one and three days. Extraction was performed by sonicating on ice five times for ten seconds each using a lysis buffer (50 mM sodium phosphate, pH 7.0, 10 mM EDTA, 0.1% TritonX-100, 0.1% sarkosyl and 10 mM β-mercaptoethanol).

Protein concentrations were determined by the BIO-RAD™ reagent protein assay (Bio-Rad Laboratories, Hercules, Calif.) according to the Bradford method. The GUS activity assay involved incubating approximately 5-10 µg of protein in the presence of 1 mM 4-methylumbelliferyl β-D-glucuronide in 100 µl of lysis buffer at 37° C. Samples from each reaction were taken at 0, 10, 20 and 40 minutes. The enzyme reaction was quenched in 0.2 M sodium carbonate ($Na_2CO_3$). The standard curve for 4-methylumbelliferon at 50, 100, 150, 200, 250, 300, 350 and 400 nM concentrations was generated with a FL600 Fluorescent Microplate Reader. The amount of 4-methylumbelliferyl β-D-glucuronide converted to 4-methylumbelliferon (MU) by GUS enzyme was determined with FL600 Fluorescent Microplate Reader and the MU standard curve. The GUS enzyme activity is expressed as pmol MU per mg protein min.

Figure 9:
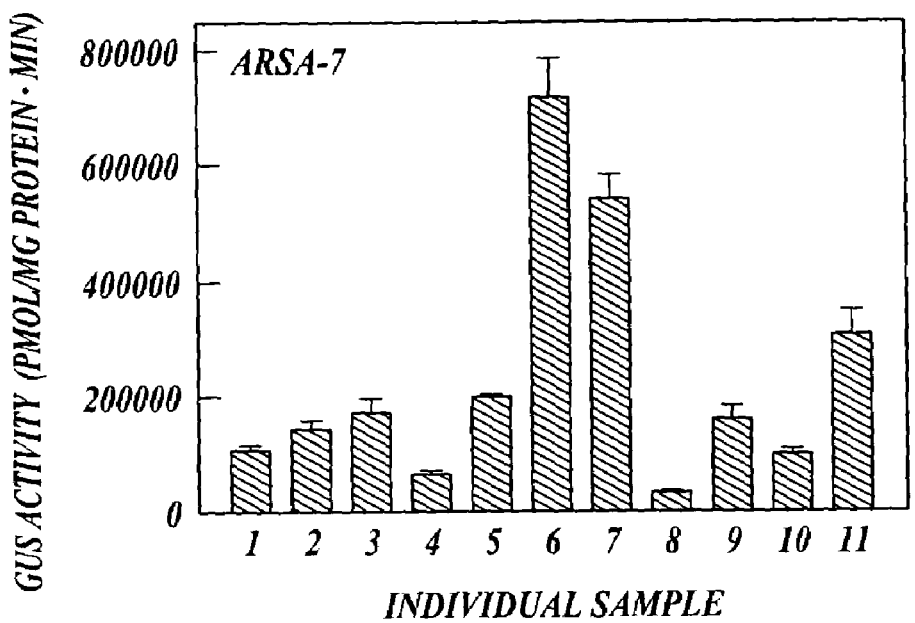
FIG. 9 is a plot of the promoter activity for a number of individual *A. niger* strains transformed with the promoter region of the pelleted-associated Arsa-7 gene (SEQ ID NO:46) and the GUS reporter gene. The promoter activity is determined via GUS activity assays and is expressed as pmol MU/mg protein/min.

Referring to FIG. 9, the expression of the GUS gene with the Arsa-7 promoter (SEQ ID NO:46) was at a high level and gradually increased under pelleted culture conditions. It remained at barely detectable levels for the first three days of growth in filamented culture conditions and then rapidly increased after three days of growth. The plot shows the activity of pelleted-enhanced Arsa-7 gene promoter (SEQ ID NO:46) in the protein extract of two days old individual transformant under pelleted growth conditions. The promoter activity is expressed at pmol MU/mg protein/min. The promoter activity in most of transgenic strains is about 200,000 pmol MU/mg protein/min. Transgenic strain No. 7 has the strongest activity among the 11 strains. The promoter activity is about four times higher than the hybrid Mac promoters that consist of the B-domain of 35S cauliflower mosaic virus promoter and the manopine synthase promoter of *Agrobacterium tumefaciens*. This activity appears to be the strongest one used in plant transgene expression. It is about 20 times higher than the yeast α-amylase promoter.

Figure 10:
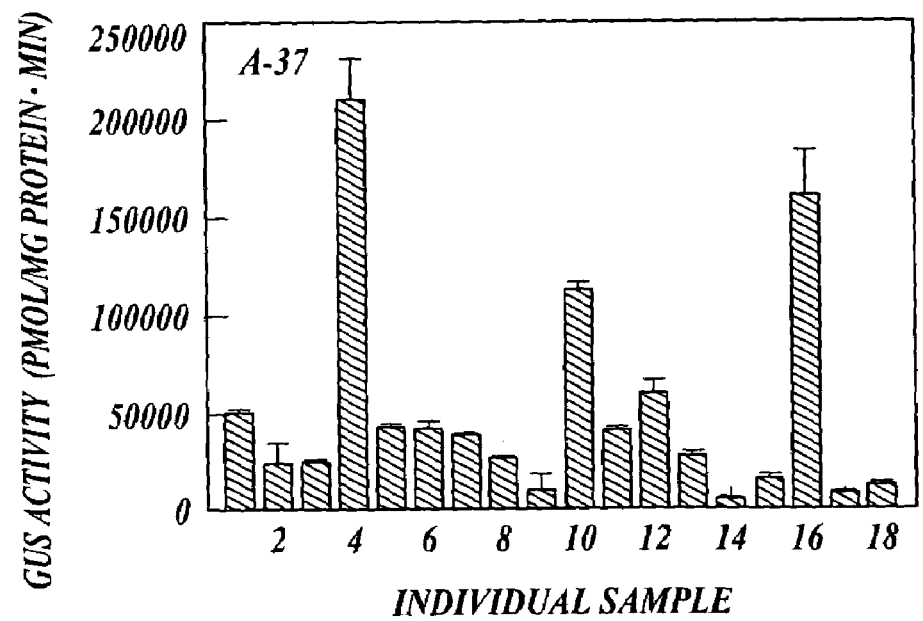
FIG. 10 is a plot of the promoter activity for a number of individual *A. niger* strains transformed with the promoter region of the pelleted-associated A-37 gene (SEQ ID NO:47) and the GUS reporter gene. The promoter activity is determined via GUS activity assays and is expressed as pmol MU/mg protein/min.

Referring to FIG. 10, the A-37 promoter (SEQ ID NO:47) activity is still higher than the yeast α-amylase and is comparable to that of the hybrid MAC promoter. The plot shows the activity of the pelleted enhanced A-37 gene promoter (SEQ ID NO: 47) in the protein extract of two days old individual transformant under pelleted growth conditions. The GUS activity of most transformants was around 50,000 pmol MU/mg protein/min, while transgenic strains 4 and 16 were about 150,000 to 200,000 pmol MU/mg protein/min. The data show that the A-37 promoter (SEQ ID NO:47) has high constitutive expression levels at pelleted culture conditions. Expression was low during the first day of growth prior to the rapid increase thereafter to the end of growth.

Figure 11:
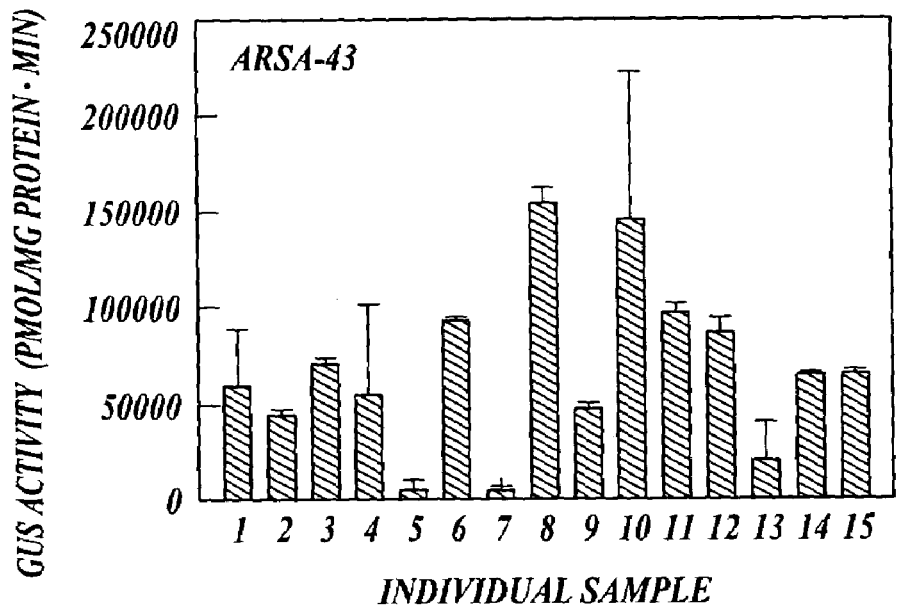
FIG. 11 is a plot of the promoter activity for a number of individual *A. niger* strains transformed with the promoter region of the pelleted-associated Arsa-43 gene (SEQ ID NO:48) and the GUS reporter gene. The promoter activity is determined via GUS activity assays and is expressed as pmol MU/mg protein/min.

Referring to FIG. 11, the Arsa-43 promoter (SEQ ID NO:48) is a polyubiquitin gene that is constitutively expressed at pelleted culture conditions. However, under filamented growth conditions its expression was low during the first day of growth, and thereafter increased rapidly to steady states for the rest of the filamented growth. Again, the plot shows the activity of the pelleted-enhanced Arsa-43 gene promoter (SEQ ID NO:48) in the protein extract of two days old individual transformant under pelleted growth conditions. For comparison purposes, the GUS activity of most transformants is around 5,000 to 10,000 pmol MU/mg protein/min.

Figure 12:
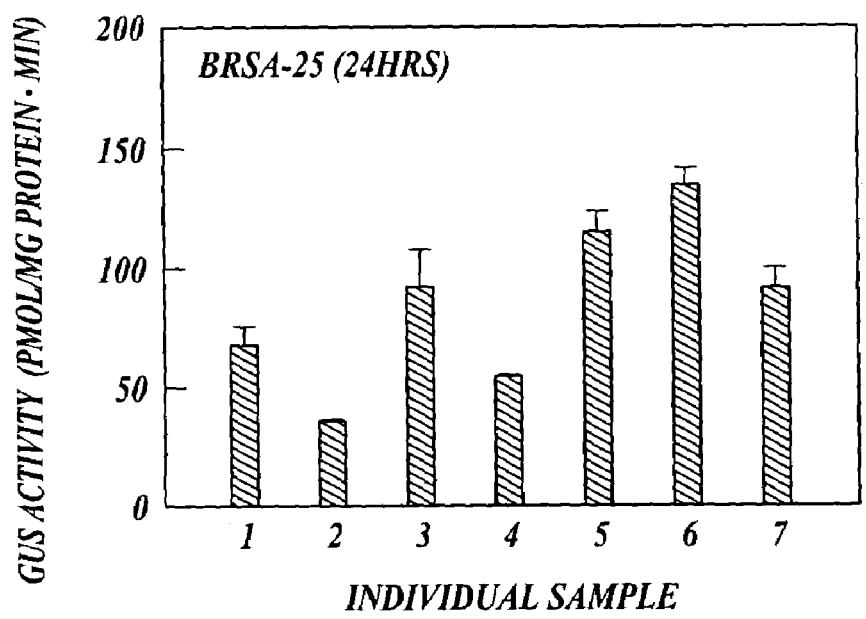
FIG. 12 is a plot of the promoter activity for a number of individual *A. niger* strains transformed with the promoter region of the filamented-associated Brsa-25 gene (SEQ ID NO:51) and the GUS reporter gene. The promoter activity is determined via GUS activity assays and is expressed as pmol MU/mg protein/min.

FIG. 12 shows the activity of filamented associated gene Brsa-25 promoter (SEQ ID NO:51) in the protein extract of two days old individual transformant under filamentous growth conditions. The GUS activity of most transformants is around 50 to 100 pmol MU/mg protein/min. The Brsa-25 promoter is filamented specific and functions temporally. Its transcription increases rapidly at the first day culture and decreases to low levels at two and three day cultures. Thereafter, its transcription augments to the level of first cultures.

Figure 13:
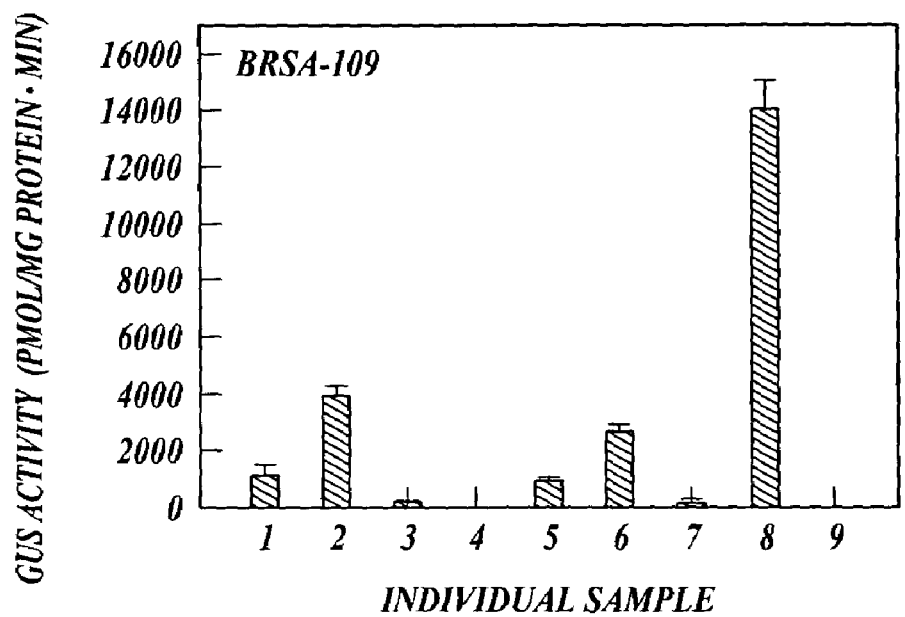
FIG. 13 is a plot of the promoter activity for a number of individual *A. niger* strains transformed with the promoter region of the filamented-associated Brsa-109 gene (SEQ ID NO:53) and the GUS reporter gene. The promoter activity is determined via GUS activity assays and is expressed as pmol MU/mg protein/min.

Referring to FIG. 13, the Brsa-109 promoter (SEQ ID NO:53) is constitutive and filamented-specific. The plot shows the activity of the filamented-enhanced Brsa-109 gene promoter in the protein extract of two days old individual transformant under filamentous growth conditions. The GUS activity of most of the transformants was around 1000 to 4000 pmol MU/mg protein/min, except transformant clone 8, which had an activity level over 14000 pmol MU/mg protein/min. The Brsa-109 gene promoter (SEQ ID NO:53) can be used for the expression of genes of interest in filamented growth conditions.

Figure 14:
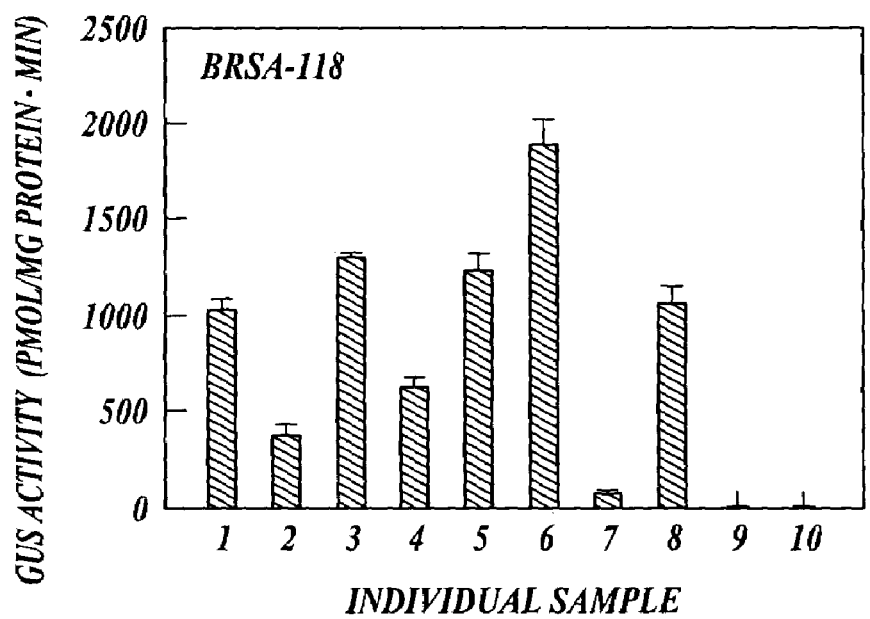
FIG. 14 is a plot of the promoter activity for a number of individual *A. niger* strains transformed with the promoter region of the filamented-associated Brsa-118 gene (SEQ ID NO:54) and the GUS reporter gene. The promoter activity is determined via GUS activity assays and is expressed as pmol MU/mg protein/min.
Figure 6:
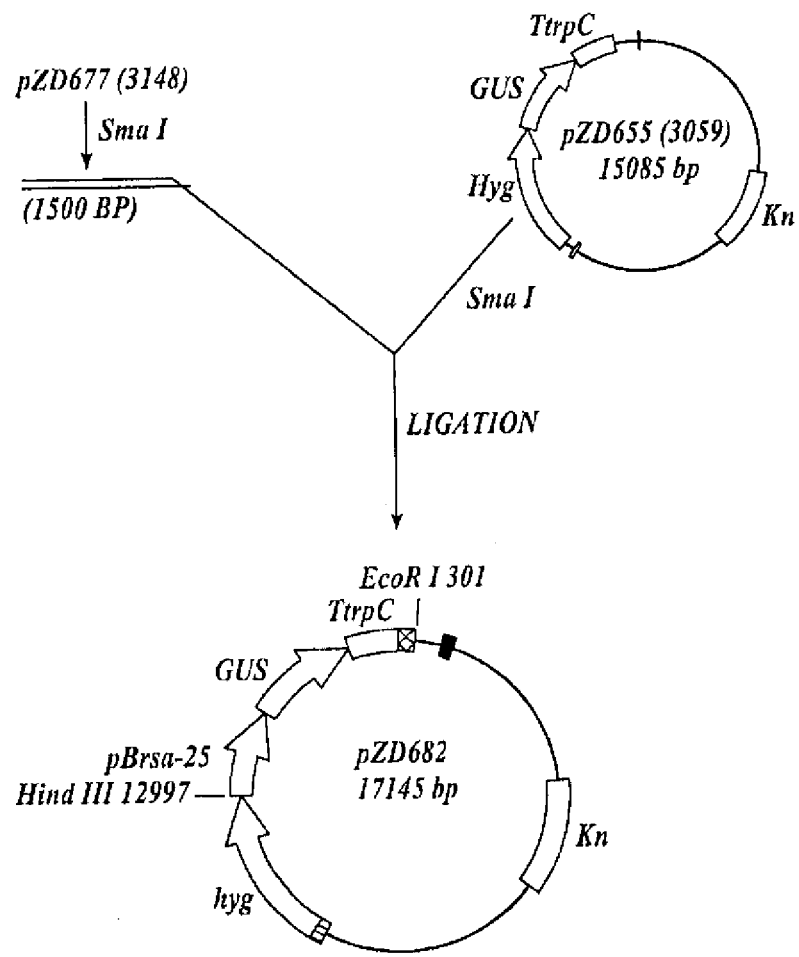

Referring to FIG. 14, the Brsa-118 promoter (SEQ ID NO:54) is temporally dependent and filamented specific, similar to the promoter of the Brsa-25 promoter (SEQ ID NO:53). The plot shows the activity of the filamented-enhanced Brsa-118 gene promoter in the protein extract of two day old individual transformant under filamentous growth conditions. The GUS activity of most transformants was around 500 to 2000 pmol MU/mg protein/min. This promoter can be used for expression of genes of interest in different developmental stages.

EXAMPLE 4

This example describes the necessary steps taken to prepare different fungal transcription terminators and insert them into the host vector pGEM-Teasy for plasmid DNA preparation. The DNA was sequenced and aligned against known DNA fragments to confirm the newly isolated transcription terminators. The transcription terminators can be used for heterologous gene expression in fungi.

The transcription terminator of the pelleted-associated Arsa-7 gene (SEQ ID NO:55) was isolated with GENOMEWALKER™ kits and gene specific primer FP-92 (SEQ ID NO:31). The genome walking libraries in Example 2 were used as template DNAs for genomic PCR with adaptor primer 1 (SEQ ID NO:35) and FP-92 primers (SEQ ID NO:31). The DNA fragments were cloned into pGEM-Teasy vector to form pZD621. The DNA sequence of the Arsa-7 gene transcription terminator (SEQ ID NO: 55) in pZD621 was determined and aligned with the known genomic DNA sequence of the Arsa-7 gene to confirm the newly isolated fragments.

The transcription terminator of the pelleted-associated A-37 gene (SEQ ID NO:56) was isolated with GENOMEWALKER™ kits and gene specific primer FP-94 (SEQ ID NO:32). The genome walking libraries in Example 2 were used as template DNAs for genomic PCR with adaptor primer 2 (SEQ ID NO:36) and FP-92 primers (SEQ ID NO:31). The DNA fragments were cloned into pGEM-Teasy vector to form pZD622. The DNA sequence of the A-37 gene transcription terminator (SEQ ID NO: 56) in pZD622 was determined and aligned with the known genomic DNA sequence of the A-37 gene to confirm the newly isolated fragments.

The transcription terminator of the pelleted-associated Arsa-43 gene (SEQ ID NO:57) was isolated with GENOMEWALKER™ kits and gene specific primer FP-100 (SEQ ID NO:33). The genome walking libraries in example 2 were used as template DNAs for genomic PCR with adaptor primer 1 (SEQ ID NO:35) and FP-100 primers (SEQ ID NO:33). The DNA fragments were cloned into pGEM-Teasy vector to form pZD615. The DNA sequence of the Arsa-43 transcription terminator (SEQ ID NO: 57) in pZD615 was determined and aligned with the known genomic DNA sequence of the Arsa-43 gene to confirm the newly isolated fragments.

The transcription terminator of pelleted-associated A-90 gene (SEQ ID NO:58) was isolated with GENOMEWALKER™ kits and gene specific primer FP-104 (SEQ ID NO:34). The genome walking libraries in example 2 were used as template DNAs for genomic PCR with adaptor primer 1 (SEQ ID NO:35) and FP-104 primers (SEQ ID NO:34). The DNA fragments were cloned into pGEM-Teasy vectors to form pZD617. The DNA sequence of the A-90 gene transcription terminator (SEQ ID NO: 58) in pZD617 was determined and aligned with the known genomic DNA sequence of the A-90 gene to confirm the newly isolated fragments.

The transcription terminator of filamented-associated Brsa-25 gene (SEQ ID NO:59) was isolated with GENOMEWALKER™ kits and gene specific primer FP-82 (SEQ ID NO:28). The genome walking libraries in example 2 were used as template DNAs for genomic PCR with adaptor primer 2 (SEQ ID NO:36) and FP-82 primers (SEQ ID NO:28). The DNA fragments were cloned into pGEM-Teasy vectors to form pZD620. The DNA sequence of the Brsa-25 gene transcription terminator (SEQ ID NO: 59) in pZD620 was determined and aligned with the known genomic DNA sequence of the Brsa-25 gene to confirm the newly isolated fragments.

The transcription terminator of filamented-associated gene Brsa-47 (SEQ ID NO:60) was isolated with GENOMEWALKER™ kits and gene specific primer FP-86 (SEQ ID NO:29). The genome walking libraries in example 2 were used as template DNAs for genomic PCR with adaptor primer 1 (SEQ ID NO:35) and FP-86 primers (SEQ ID NO:29). The DNA fragments were cloned into pGEM-Teasy vectors to form pZD626. The DNA sequence of the Brsa-47 gene transcription terminator (SEQ ID NO: 60) in pZD626 was determined and aligned with the known genomic DNA sequence of the Brsa-47 gene to confirm the newly isolated fragments.

The transcription terminator of filamented-associated Brsa-118 gene (SEQ ID NO:61) was isolated with GENOMEWALKER™ kits and gene specific primer FP-90 (SEQ ID NO:30). The genome walking libraries in example 2 were used as template DNAs for genomic PCR with adaptor primer 1 (SEQ ID NO:35) and FP-90 primers (SEQ ID NO:30). The DNA fragments were cloned into pGEM-Teasy vectors to form pZD627. The DNA sequence of Brsa-118 gene transcription terminator (SEQ ID NO: 61) in pZD627 was determined and aligned with the known genomic DNA sequence of the Brsa-118 gene to confirm the newly isolated fragments.

While a number of embodiments of the present invention have been shown and described, it will be apparent to those skilled in the art that many changes and modifications may be made without departing from the invention in its broader aspects. The appended claims, therefore, are intended to cover all such changes and modifications as they fall within the true spirit and scope of the invention.

We claim:

1. An isolated polynucleotide molecule comprising a polynucleotide sequence that regulates expression of a gene comprising at least one of SEQ ID NOs 46 and 55, wherein said gene is differentially expressed in a native fungus exhibiting a pellet morphology relative to said native fungus exhibiting a filament morphology and wherein said isolated polynucleotide molecule is combined with a molecule comprising a coding region of a foreign gene for heterologous gene expression.

2. The isolated polynucleotide molecule as recited in claim 1, wherein said expression is constitutive in said native fungus exhibiting said pellet morphology.

3. The isolated polynucleotide molecule as recited in claim 1, wherein said expression initiates at a developmental stage in said native fungus exhibiting said filament morphology.

4. The isolated polynucleotide molecule as recited in claim 1, wherein said expression is constitutive in said native fungus exhibiting said filament morphology.

5. The isolated polynucleotide molecule as recited in claim 1, wherein said native fungus is *Aspergillus niger*.

6. An isolated polynucleotide molecule comprising a polynucleotide transcription terminator SEQ ID NO. 55 wherein said isolated polynucleotide molecule is combined with a molecule comprising a foreign gene for heterologous gene expression.

7. The isolated polynucleotide molecule as recited in claim 6, wherein said native fungus is *Aspergillus niger*.

8. An isolated polynucleotide molecule comprising a promoter functional in fungi, wherein said promoter comprises at least of SEQ ID NO.:46.

9. An isolated polynucleotide molecule comprising a transcription terminator, wherein said transcription terminator is a functional terminator comprising SEQ ID NO.:55.

10. A DNA construct comprising the following elements operably linked in the direction of transcription:
   a. a first DNA segment comprising SEQ ID NO.:46,
   b. a second DNA segment comprising a sequence coding a protein of interest, the second DNA segment being heterologous relative to the functional promoter; and
   c. a third DNA segment comprising a functional transcription terminator.

11. The DNA construct as recited in claim 10, wherein said transcription terminator comprises SEQ ID NO.:55.

12. The DNA construct as recited in claim 10, wherein said second DNA segment comprises a coding sequence that is differentially expressed in a native fungus exhibiting a pellet morphology relative to said native fungus exhibiting a filament morphology.

13. A vector comprising the DNA construct of claim 10.

14. The vector as recited in claim 13, wherein said second DNA segment comprises a coding sequence for GUS.

15. A transformed host cell comprising the DNA construct of claim 10.

16. The transformed host cell as recited in claim 15, wherein said transformed host cell constitutively expresses said second DNA segment.

17. The transformed host cell as recited in claim 15, wherein expression of said second DNA segment by said transformed host cell is temporally-regulated or spatially-regulated.

18. The transformed host cell comprising the DNA construct of claim 15, wherein said functional transcription terminator is SEQ ID NO.:55.

* * * * *

UNITED STATES PATENT AND TRADEMARK OFFICE
CERTIFICATE OF CORRECTION

| | |
|---|---|
| PATENT NO. | : 7,449,569 B2 |
| APPLICATION NO. | : 10/920625 |
| DATED | : November 11, 2008 |
| INVENTOR(S) | : Dai et al. |

It is certified that error appears in the above-identified patent and that said Letters Patent is hereby corrected as shown below:

Delete drawing sheet 11/16 and replace with the drawing sheet 11/16 attached.

Column 5, Line 38 – Replace "DraI, EcoRV, PuvII, or StuI" with --Dra I, EcoR V, Puv II, or Stu I--.

Signed and Sealed this

Twenty-first Day of April, 2009

JOHN DOLL
*Acting Director of the United States Patent and Trademark Office*